(12) United States Patent
Ning et al.

(10) Patent No.: US 11,554,266 B2
(45) Date of Patent: Jan. 17, 2023

(54) FIXING DEVICE OF WIRELESS CHARGER AND WIRELESS CHARGING DEVICE

(71) Applicant: SCENERAY CO., LTD., Suzhou (CN)

(72) Inventors: Yihua Ning, Suzhou (CN); Fan Zhang, Suzhou (CN); Minfang Gao, Suzhou (CN)

(73) Assignee: SCENERAY CO., LTD., Suzhou (CN)

( * ) Notice: Subject to any disclaimer, the term of this patent is extended or adjusted under 35 U.S.C. 154(b) by 265 days.

(21) Appl. No.: 16/772,795

(22) PCT Filed: Dec. 12, 2018

(86) PCT No.: PCT/CN2018/120494
§ 371 (c)(1),
(2) Date: Jun. 14, 2020

(87) PCT Pub. No.: WO2019/114734
PCT Pub. Date: Jun. 20, 2019

(65) Prior Publication Data
US 2021/0162221 A1 Jun. 3, 2021

(30) Foreign Application Priority Data

Dec. 14, 2017 (CN) .......................... 201711341212.6
Dec. 4, 2018 (CN) .......................... 201811474609.7

(51) Int. Cl.
*A61N 1/37* (2006.01)
*A61N 1/378* (2006.01)
(Continued)

(52) U.S. Cl.
CPC ........... *A61N 1/3787* (2013.01); *A61N 1/375* (2013.01); *H02J 50/005* (2020.01); *H02J 50/10* (2016.02); *H02J 2310/23* (2020.01)

(58) Field of Classification Search
CPC .............................. A61N 1/375; A61N 1/3787
See application file for complete search history.

(56) References Cited

U.S. PATENT DOCUMENTS 3,942,535 A * 3/1976 Schulman ............... H02J 50/70
607/33
5,991,665 A * 11/1999 Wang ...................... H02J 7/025
320/108
(Continued)

FOREIGN PATENT DOCUMENTS

CN 204218197 U 3/2015
CN 205516007 U 8/2016
(Continued)

*Primary Examiner* — Eric D. Bertram
(74) *Attorney, Agent, or Firm* — Cheng-Ju Chiang

(57) ABSTRACT

The present invention discloses a fixing device of a wireless charger for an implanted medical device, wherein the fixing device comprising a supporting member wearable on a patient's body and an adjustment structure connected to the supporting member, a charger fixing seat is connected to one of the supporting member and the adjustment structure, the adjustment structure comprises an adjustment strap and a fixing buckle engaging with the adjustment strap, one end of the adjustment strap is connected to the supporting member, the other end of the adjustment strap operably brings the supporting member or the charger fixing seat to be adjusted to a position where the charger fixing seat corresponds to the implanted medical device, and a position where the adjustment strap engages with the fixing buckle can be adjusted and locked.

17 Claims, 17 Drawing Sheets

(51) Int. Cl.
*H02J 50/00* (2016.01)
*A61N 1/375* (2006.01)
*H02J 50/10* (2016.01)

(56) References Cited

U.S. PATENT DOCUMENTS

| | | | |
|---|---|---|---|
| 8,612,015 B2 | 12/2013 | Knifong, Sr. | |
| 8,706,255 B2 | 4/2014 | Phillips et al. | |
| 2005/0288743 A1* | 12/2005 | Ahn | A61N 1/3787 607/61 |
| 2007/0255223 A1 | 11/2007 | Phillips et al. | |
| 2009/0251101 A1 | 10/2009 | Phillips et al. | |
| 2011/0166630 A1* | 7/2011 | Phillips | A61N 1/3787 607/61 |
| 2017/0296833 A1 | 10/2017 | Jaax et al. | |

FOREIGN PATENT DOCUMENTS

| | | |
|---|---|---|
| CN | 107349525 A | 11/2017 |
| WO | 2009/123780 A1 | 10/2009 |

* cited by examiner

FIXING DEVICE OF WIRELESS CHARGER AND WIRELESS CHARGING DEVICE

The present application is a 35 U.S.C. § 371 National Phase conversion of International (PCT) Patent Application No. PCT/CN2018/120494, filed on Dec. 12, 2018, which claims priority to Chinese Patent Application No. 201711341212.6, filed to the Chinese Patent Office on Dec. 14, 2017 and titled "Fixing Device of Wireless Charger and Wireless Charging Device", and Chinese Patent Application No. 201811474609.7, filed to the Chinese Patent Office on Dec. 4, 2018 and titled "Fixing Device of Wireless Charger and Wireless Charging Device" the content of which is incorporated herein by reference in its entirety. The PCT International Patent Application was filed and published in Chinese.

TECHNICAL FIELD

The present invention relates to a fixing device of a wireless charger, particularly to a fixing device of a wireless charger for charging a rechargeable implantable medical device, and a wearable wireless charging device.

BACKGROUND

Implantable medical devices are diverse and applied in a wide scope, for example, cardiac pacemakers and spinal cord stimulators, and implantable neurostimulators. The implantable medical products available in the market are mostly powered by high-energy-density lithium primary batteries, and mostly have a shorter service life. In recent years, along with the development of wireless technologies and lithium rechargeable battery technologies, developing implantable rechargeable medical devices with a longer service life has become a mainstream future development tendency.

The implantable medical devices are implanted into a patient's body and isolated from an in vitro charging device by a tissue such as skin, and they need to be charged wirelessly and percutaneously. The charging manner is generally based on an electromagnetic coupling principle, and an electromagnetic field is used to penetrate the patient's skin to transfer energy to the implanted medical device. Upon charging, a charging coil needs to be accurately and stably align with the implanted stimulator. If there is not an assistant tool, the patient needs to be hold the coil close to the chest motionlessly for one hour or a longer period of time while charging, which is a painful thing and very difficult to complete by the patient. Furthermore, misalignment is likely to be caused without notice, which will cause a lower charging efficiency even failure to charge.

A fixing device of a portable wireless charger in the prior art is a shoulder strap form and includes a shoulder strap portion, a host sheath and a coil sheath. The shoulder strap is worn on the patient's body, and the charging coil and charger are placed in the coil sheath and host sheath respectively. Such a portable charging device has problems such as inconvenient wearing and detachment, and cannot be conveniently used by the patient.

In view of the above problems, it is necessary to make further improvements with respect to drawbacks in the prior art.

SUMMARY

An object of the present invention is to provide a fixing device of a wireless charger for charging a rechargeable implanted medical device. The fixing device of the wireless charger is simple to wear and quick and convenient to put on and put off.

To achieve the above object, the present invention provides a fixing device of a wireless charger for an implanted medical device, wherein the fixing device comprises a supporting member wearable on a patient's body and an adjustment structure connected to the supporting member, a charger fixing seat is connected to one of the supporting member and the adjustment structure, the adjustment structure comprises an adjustment strap and a fixing buckle engaging with the adjustment strap, one end of the adjustment strap is connected to the supporting member, the other end of the adjustment strap operably brings the supporting member or the charger fixing seat to be adjusted to a position where the charger fixing seat corresponds to the implanted medical device, and a position where the adjustment strap engages with the fixing buckle can be adjusted and locked.

As a further improvement of the embodiment of the present invention, wherein the charger fixing seat is connected to the supporting member, one end of the fixing buckle is fixed on the supporting member, and the other end of the fixing buckle is movably connected to the adjustment strap.

As a further improvement of the embodiment of the present invention, wherein the fixing buckle comprises a male snap and a female snap which are detachably connected, and the male snap and female snap are respectively connected to the supporting member and the adjustment strap.

As a further improvement of the embodiment of the present invention, wherein the supporting member comprises a left connecting portion and a right connecting portion, bottom sides of a front portion of the supporting member and a rear portion of the supporting member are connected via the left connecting portion and the right connecting portion, one of the left connecting portion and the right connecting portion is used to form a shoulder cuff to be supported under the patient's armpit, the other of the left connecting portion and right connecting portion is configured as the adjustment strap, one end of the adjustment strap is connected to the rear portion of the supporting member, and the fixing buckle is connected between the front portion of the supporting member and the adjustment strap.

As a further improvement of the embodiment of the present invention, wherein a shoulder portion of the supporting member and one of the left connecting portion and the right connecting portion are both configured as elastic extensible belts.

As a further improvement of the embodiment of the present invention, wherein the charger fixing seat is configured as a storage bag, and the storage bag is connected between the shoulder of the supporting member and the front portion of the supporting member.

As a further improvement of the embodiment of the present invention, wherein the storage bag comprises an outer bag located outside and an inner bag located inside, a partition layer is disposed between the outer bag and inner bag, and the shoulder portion of the supporting member is connected to the partition layer.

As a further improvement of the embodiment of the present invention, wherein the storage bag comprises an outer bag located outside and an inner bag located inside, and the outer bag is communicated with the inner bag.

As a further improvement of the embodiment of the present invention, wherein the storage bag is made of a mesh-like fabric.

As a further improvement of the embodiment of the present invention, wherein a female hook-and-loop fastener belt is disposed on one of an outer side of the storage bag and an inner side of the storage bag, a male hook-and-loop fastener belt having a fluffy surface is disposed on the other of the outer side of the storage bag and inner side of the storage bag, and the female hook-and-loop fastener belt separably engages with the male hook-and-loop fastener belt to close at least one portion of a bag mouth of the storage bag.

As a further improvement of the embodiment of the present invention, wherein one of an outer side of the storage bag and a shoulder portion of the supporting member is provided with a female hook-and-loop fastener belt, the other of the outer side of the storage bag and the shoulder portion of the supporting member is provided with a male hook-and-loop fastener belt having a fluffy surface, and the female hook-and-loop fastener belt separably engages with the male hook-and-loop fastener belt to close at least one portion of a bag mouth of the storage bag.

As a further improvement of the embodiment of the present invention, wherein a front portion of the supporting member consists of an inner layer and an outer layer, and at least partial edge of the charger fixing seat is connected between the inner layer and outer layer.

As a further improvement of the embodiment of the present invention, wherein the charger fixing seat is disposed on the adjustment strap, one end of the adjustment strap is connected to a shoulder portion or a rear portion of the supporting member, the other end of the adjustment strap operably brings the charger fixing seat to be adjusted to a position where the charger fixing seat corresponds to the implanted medical device, and the other end of the adjustment strap can be adjusted and locked at the front portion of the supporting member.

As a further improvement of the embodiment of the present invention, wherein the supporting member comprises a shoulder portion of the supporting member, bottom sides of a front portion of the supporting member and a rear portion of the supporting member are connected via the left connecting portion and the right connecting portion, the left connecting portion and the right connecting portion are used to form a shoulder cuff to be supported under the patient's armpit, one end of the adjustment strap is connected to the shoulder portion of the supporting member or the rear portion of the supporting member, and the other end of the adjustment strap is adjusted and locked at the front portion of the supporting member.

As a further improvement of the embodiment of the present invention, wherein the front portion of the supporting member is provided with a charging opening, the charging opening corresponds to a position of the implanted medical device, and the charger fixing seat can be adjusted in the charging opening.

As a further improvement of the embodiment of the present invention, wherein the adjustment strap comprises a positioning strap connecting the shoulder portion of the supporting member or the rear portion of the supporting member and the charger fixing seat and a fixing strap connecting the charger fixing seat with the front portion of the supporting member, and the fixing strap can be adjusted and locked at the front portion of the supporting member.

As a further improvement of the embodiment of the present invention, wherein the positioning strap is configured as an elastic extensible belt or provided with a length adjuster, and the length adjuster moves in a lengthwise direction of the positioning strap to adjust a distance between a connection end of the positioning strap connected to the supporting member and the charger fixing seat.

As a further improvement of the embodiment of the present invention, wherein the fixing buckle comprises a female hook-and-loop fastener belt and a male hook-and-loop fastener belt engaging therewith and having a fluffy surface, the female hook-and loop fastener belt is disposed on one of the fixing strap and the front portion of the supporting member, the male hook-and-loop fastener belt is disposed on the other of the fixing strap and the front portion of the supporting member, and the fixing strap is adjusted and locked through the separable engagement of the female hook-and-loop fastener belt and the fluffy surface to adjust the position of the charger fixing seat.

As a further improvement of the embodiment of the present invention, wherein the positioning strap is connected to a middle portion of the rear portion of the supporting member via a fixing snap and is rotatable relative to the supporting member.

As a further improvement of the embodiment of the present invention, wherein the positioning strap is separably engaged to the shoulder supporting portion or the rear portion of the supporting member, and the engagement position can be adjusted.

As a further improvement of the embodiment of the present invention, wherein the front portion of the supporting member comprises a left front sheet and a right front sheet, and the left front sheet and right front sheet are both provided with a charging opening and separably connected.

As a further improvement of the embodiment of the present invention, wherein the left front sheet and right front sheet are partially overlapped, and connected in a hook-and-loop manner.

As a further improvement of the embodiment of the present invention, wherein an outer side of one of the left front sheet and right front sheet is provided with a first male hook-and-loop fastener belt having a fluffy surface, an inner side of the other of the left front sheet and right front sheet is provided with a female hook-and-loop fastener belt engaging with the fluffy surface, an outer side is provided with a second male hook-and-loop fastener belt having the fluffy surface, and the other end of the adjustment strap is separably connected to the second male hook-and-loop fastener belt.

The present invention also provides a wireless charging device, wherein the wireless charging device comprising a wireless charger and the fixing device of the wireless charger according to one of the embodiments above, the wireless charger is detachably mounted to the charger fixing seat, and the wireless charger can generate a charging field to charge the implanted medical device.

As compared with the prior art, the advantageous effects of the present invention are as follows: the fixing device of the wireless charger is configured as a wearable supporting member having a vest structure so that the charger can be held close to the patient's body and the patient can use it conveniently. Furthermore, the use of the fixing device of the wireless charger substantially reduces the processing steps in charging the rechargeable pulse-type generator.

BRIEF DESCRIPTION OF THE DRAWINGS

Some specific embodiments of the present disclosure will be described later in detail in an exemplary and unrestrictive

DETAILED DESCRIPTION

The present invention will be described in detail below in conjunction with specific embodiments shown in the figures. However, these embodiments are not intended to limit the present invention. Structural, methodological or functional variations made by those having ordinary skill in the art according to these embodiments are all included in the protection scope of the present invention.

The fixing device of the wireless charger according to the present invention is used to charge the rechargeable implantable medical device. The rechargeable implantable medical device is adapted for an implantable deep brain stimulation system (DBS) or other similar stimulation systems. The rechargeable implantable medical device is implanted into a patient body upon use and used to apply a pulse electrical stimulation to the patient.

Figure 1:
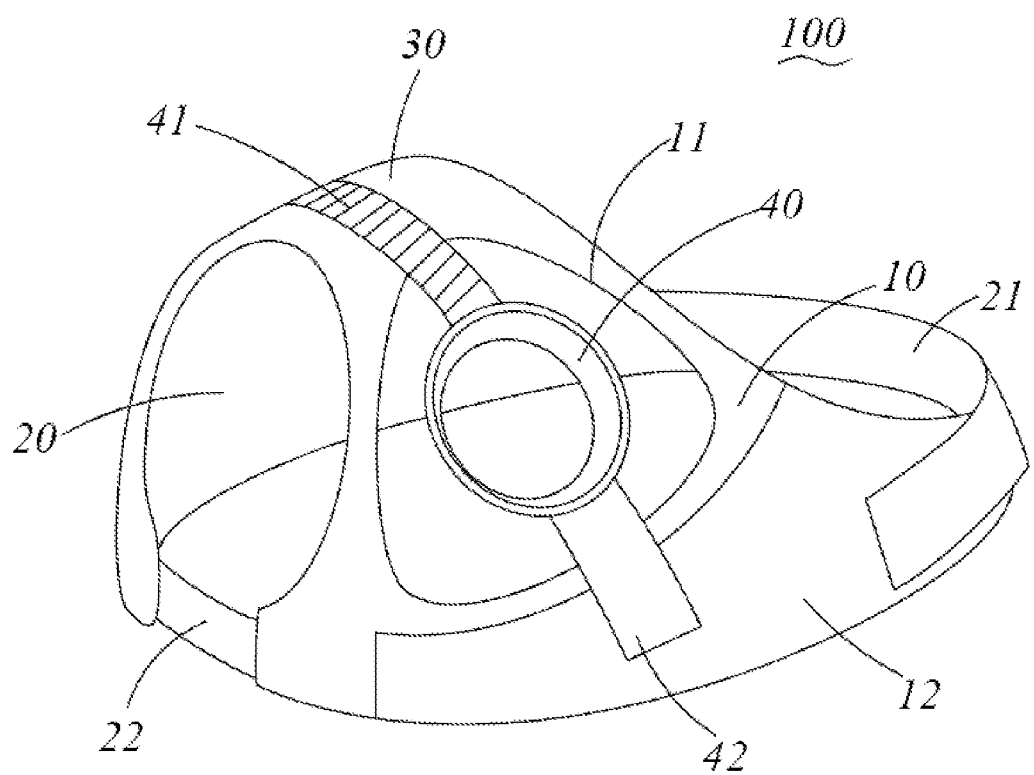
FIG. 1 is a perspective view of a fixing device of a wireless charger in a first preferred embodiment of the present invention.
Figure 2:
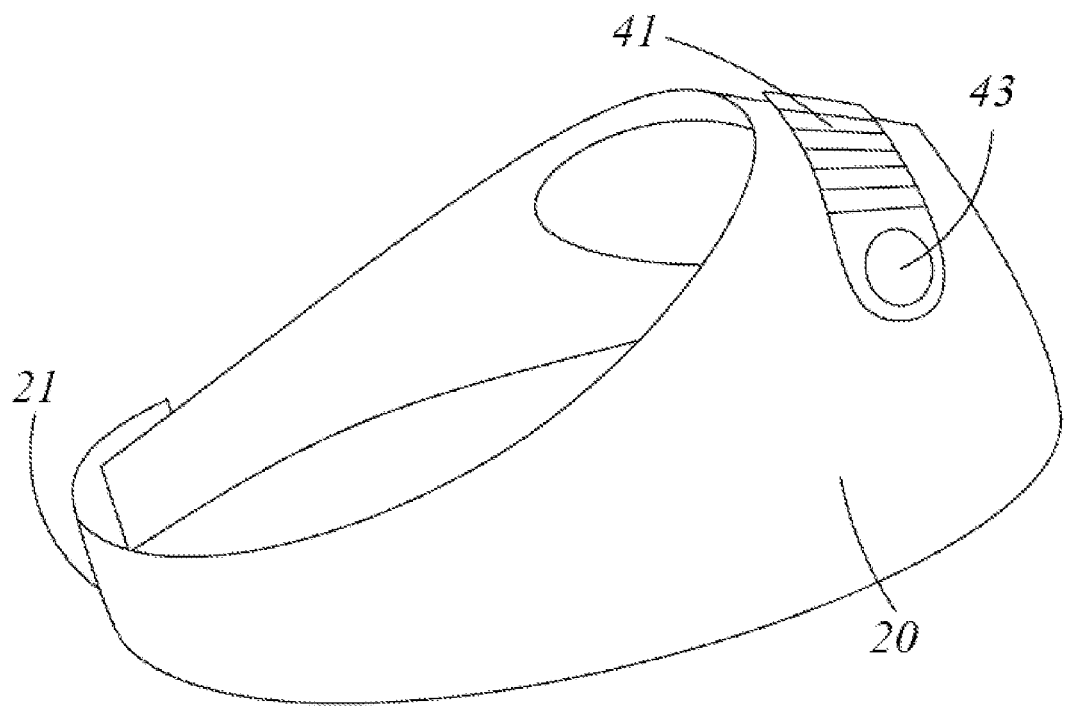
FIG. 2 is a perspective view of the fixing device of FIG. 1 as viewed from another aspect.

FIG. 1 and FIG. 2 show a first preferred embodiment of the fixing device of the wireless charger according to the present invention. The fixing device 100 of the wireless charger comprises a supporting member wearable on a patient's body and an adjustment structure connected to the supporting member, the supporting member employing a wearable supporting member such as a supporting member with a vest structure. A charger fixing seat 40 is connected to one of the supporting member and the adjustment structure. The adjustment structure comprises an adjustment strap and a fixing buckle engaging with the adjustment strap, one end of the adjustment strap is connected to the supporting member, the other end of the adjustment strap operably brings the supporting member or the charger fixing seat to be adjusted to a position where the charger fixing seat corresponds to the implantable medical device, and the position where the adjustment strap engages with the fixing buckle is fixed relative to the supporting member.

In the present embodiment, the charger fixing seat 40 is disposed on the adjustment strap, one end of the adjustment strap is connected to a shoulder portion or rear portion of the supporting member, and the other end of the adjustment strap operably brings the charger fixing seat to be adjusted to the position where the charger fixing seat corresponds to the implantable medical device, and is separably fastened to a front portion of the supporting member. The shoulder portion of the supporting member refers to a portion close to the patient's shoulder when the supporting member is worn on the patient's body. Likewise, the rear portion of the supporting member refers to a portion close to the patient's back when the supporting member is worn on the patient's body. The front portion of the supporting member refers to a portion close to the patient's chest when the supporting member is worn on the patient's body. Specifically, the supporting member comprises a shoulder supporting portion 30, and a front sheet 10 and a rear sheet 20 respectively connected to the front and rear of the shoulder supporting portion 30. The shoulder supporting portion 30 is a portion close to the patient's shoulder when the supporting member is worn on the patient's body and may be regarded as the shoulder portion of the supporting member; the front sheet 10 is a portion close to the patient's chest when the supporting member is worn on the patient's body and may be regarded as the front portion of the supporting member; the rear sheet 20 is a portion close to the patient's back when the supporting member is worn on the patient's body and may be regarded as the rear portion of the supporting member. Bottom sides of the front sheet 10 and the rear sheet 20 are connected via a left connecting portion 21 and a right connecting portion 22. The left connecting portion 21 and the right connecting portion 22 are used to form a shoulder cuff to be supported under the patient's armpit. One end of the adjustment strap is connected to the shoulder supporting portion 30 or the rear sheet 20 of the shoulder supporting member. The front sheet 10 is provided with a charging opening 11. The other end of the adjustment strap operably brings the charger fixing seat 40 to be adjusted to a position in the charging opening 11 corresponding to the implantable medical device, that is to say, the charging opening 11 corresponds to the position of the implantable medical device.

In the present embodiment, the fixing buckle comprises a female hook-and-loop fastener belt and a male hook-and-loop fastener belt engaging therewith and having a fluffy surface. The female hook-and-loop fastener belt is disposed on one of the adjustment strap and the front sheet 10, and the male hook-and-loop fastener belt is disposed on the other of the adjustment strap and the front sheet 10. The adjustment strap is fixed through the separable engagement of hook-and-loop and fluffy surface to adjust the position of the charger fixing seat 40. In addition, the shoulder supporting portion 30 and the front sheet 10 and rear sheet 20 are directly connected together, and preferably the shoulder supporting portion 30 and the front sheet 10 and rear sheet 20 are an integral structure. Certainly, in other implementable solutions, the shoulder supporting portion 30 may also be configured to be an extensible belt, i.e., the front sheet 10 and rear sheet 20 are indirectly connected via a telescopic belt. In addition, the front 10 and rear sheet 20 may also be disposed symmetrical relative to the shoulder supporting portion 30 to facilitate manufacture. The supporting member is entirely constructed as a single-shoulder vest structure, i.e., only one shoulder supporting portion 30 is provided, namely, the shoulder supporting portion 30 on the right side. The charging opening 11 may be disposed on one side with the shoulder supporting portion 30.

The left connecting portion 21 may also be configured as a belt integral with the rear sheet, and it may have a free end on which is provided a second female hook-and-loop fastener belt. The front sheet 10 is provided with a male hook-and-look fastener belt having a fluffy surface 12. The free end of the left connecting potion 21 may be adjusted according to the patient's body to a suitable position to engage with the fluffy surface 12 of the front sheet 10. The fluffy surface 12 is configured to be strip-shaped, triangular or arcuate and continuously distributed along the lower side of the front sheet. The fluffs of the fluffy surface are formed of fabric with fine fluffs protruding. The fine fluffs have tiny protrusions which are in the shape of short fluffs or pointed fluffs or fingers or branches or loops or honeycombs. The right connecting portion 22 may be configured to be an extensible connecting portion made of an extensible material or extensible structure, and may also be a belt shape. Both ends of the right connecting portion 22 are respectively connected to the front sheet 10 and rear sheet 20, and the right connecting portion 22 may be adjusted through its own extensibility to adapt to different human bodies. The left connecting portion 21 and right connecting portion 22 may be configured to be the same or different structures.

Furthermore, the adjustment strap comprises a positioning strap 41 connected to a shoulder supporting portion 30 or rear sheet 20 and a fixing strap 42. In the present embodiment, the positioning strap 41 is connected to the shoulder supporting portion 30 or a position of the rear sheet 20 adjacent to the shoulder supporting portion 30. The fixing strap 42 is configured as the other end of the adjustment strap. The fixing strap 42 is separably connected to the front sheet 10. A preferable female hook-and-loop fastener belt may be disposed on the fixing strap 42 and engage with the fluffy surface 12 on the front sheet 10. The positioning strap 41 and fixing strap 42 are respectively connected at opposite sides of the fixing seat 40. Furthermore, the positioning strap 41 and fixing strap 42 may be arranged to detachably connect with the fixing seat. The shape of the fixing seat matches that of the wireless charger to facilitate the wireless charger to be mounted and held to the fixing seat. The end of the positioning strap 41 connected to the shoulder supporting portion 30 or rear sheet 20 is connected via a fixing snap 43 disposed on the shoulder supporting portion 30 or rear sheet 20 so that the positioning strap 41 can be adjusted relative to the position of the supporting member.

In addition, to mount the wireless charger on the charger fixing seat more reliably, an elastic band for retaining the wireless charger may be disposed on the charger fixing seat. For example, the elastic band may be hooked to both sides of the charger fixing seat to limit the displacement of the wireless charger.

Figure 3:
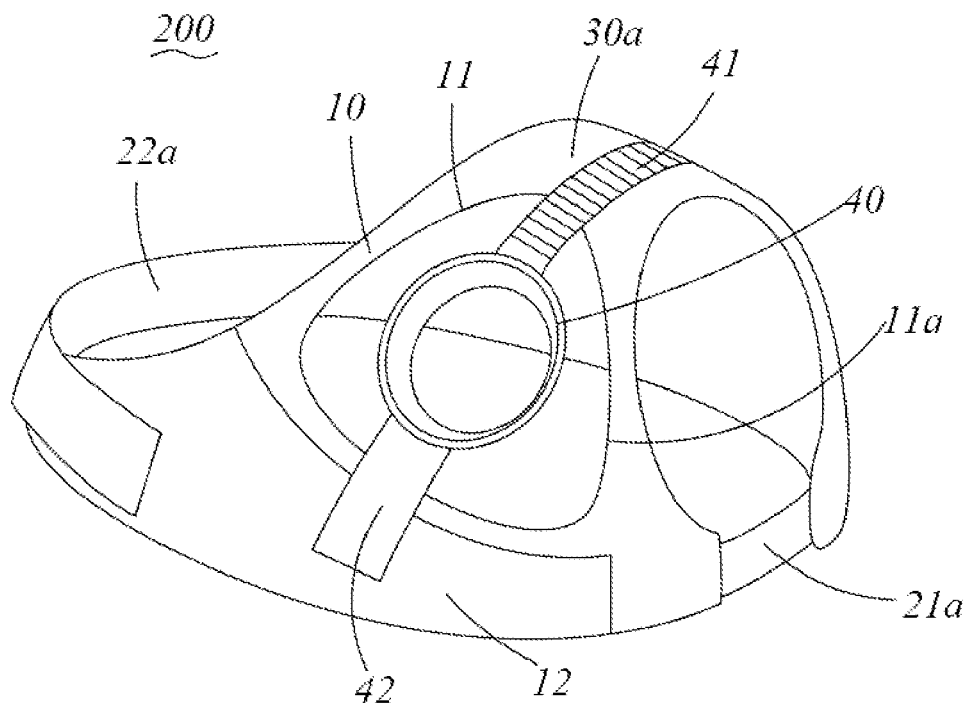
FIG. 3 is a perspective view of a fixing device of a wireless charger in a second preferred embodiment of the present invention.
Figure 4:
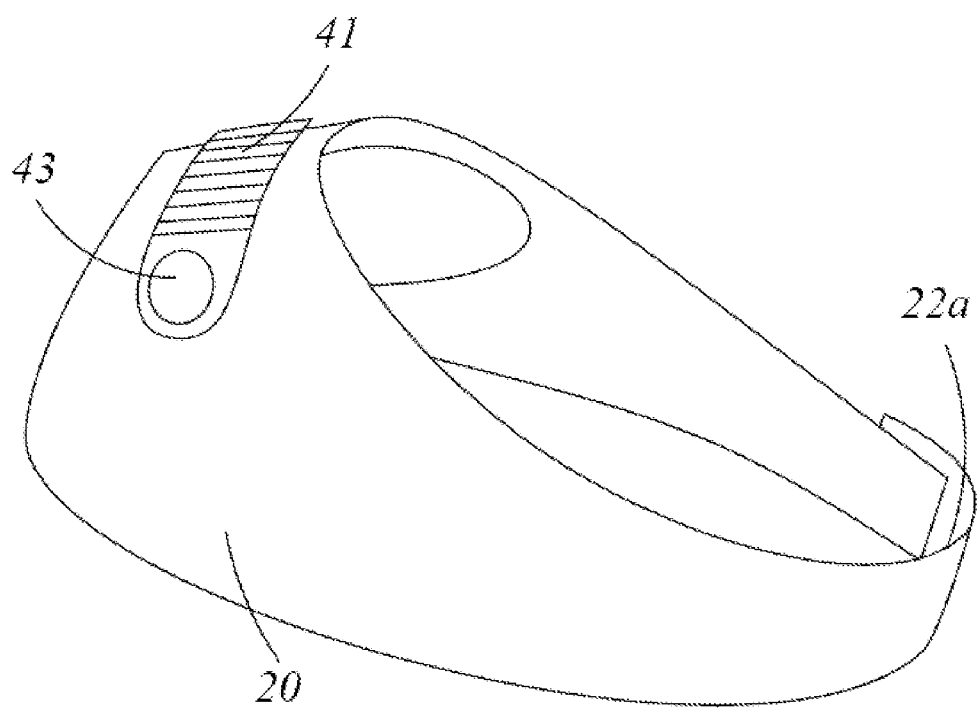
FIG. 4 is a perspective view of the fixing device of FIG. 3 as viewed from another aspect.

FIG. 3 and FIG. 4 show a second preferred embodiment of the fixing device of the wireless charger of the present invention. Components of the fixing device 200 of the wireless charger which are denoted with the same reference numbers as the first embodiment have the same structures and functions and will not be described in detail any more. Different from the first embodiment, one shoulder supporting portion is disposed as the shoulder supporting portion 30a on the left side. A left connecting portion 21a in the present embodiment is structurally similar to the right connecting portion 22 in the first embodiment, and a right connecting portion 22a is structurally similar to the left connecting portion 21 in the first embodiment. A charging opening 11a is disposed on the left side of the supporting member. That is to say, the fixing device 100 in the first embodiment and the fixing device 200 in the second embodiment may be regarded as symmetrical structures.

According to the above two embodiments, the supporting member structured as a single vest may be disposed as left-side single-shoulder or right-side single-shoulder. The left connecting portion and right connecting portion are structured the same and interchangeable. The female hook-and-loop fastener belt and the male hook-and-loop fastener belt having the fluffy surface 12 may also be disposed interchangeable, i.e., the front sheet 10 is provided with the female hook-and-loop fastener belt, and free ends of the fixing strap 42, the left connecting portion 21 and right connecting potion 22a are provided with the male hook-and-loop fastener belt engaging with the female hook-and-loop fastener belt and having the fluffy surface, which all can be implemented. Certainly, the interchange of the left-side single-shoulder or right-side single-shoulder may also be implemented through one of single-shoulder structural forms, e.g., the supporting member may be arranged to be wearable from inside or outside so that the left-shoulder vest may be worn reversely as the right-shoulder vest. As such, the male hook-and-loop fastener belt having the fluffy surface 12 may be disposed on inner and outer sides of the front sheet, and preferably disposed at the lower side of the front sheet. The inner and outer sides of the left connecting portion 21 or right connecting portion 22a are both provided with the female hook-and-loop fastener belt engaging with the fluffy surface 12. Furthermore, the inner and outer sides of the fixing strap 42 may also be provided with the female hook-and-loop fastener belt to engage with the fluffy surface 12. In addition, the fixing snap 43 may also be disposed on both inner and outer sides of the supporting member so that the positioning strap 41 can be conveniently connected when the supporting member is worn reversely.

Figure 5:
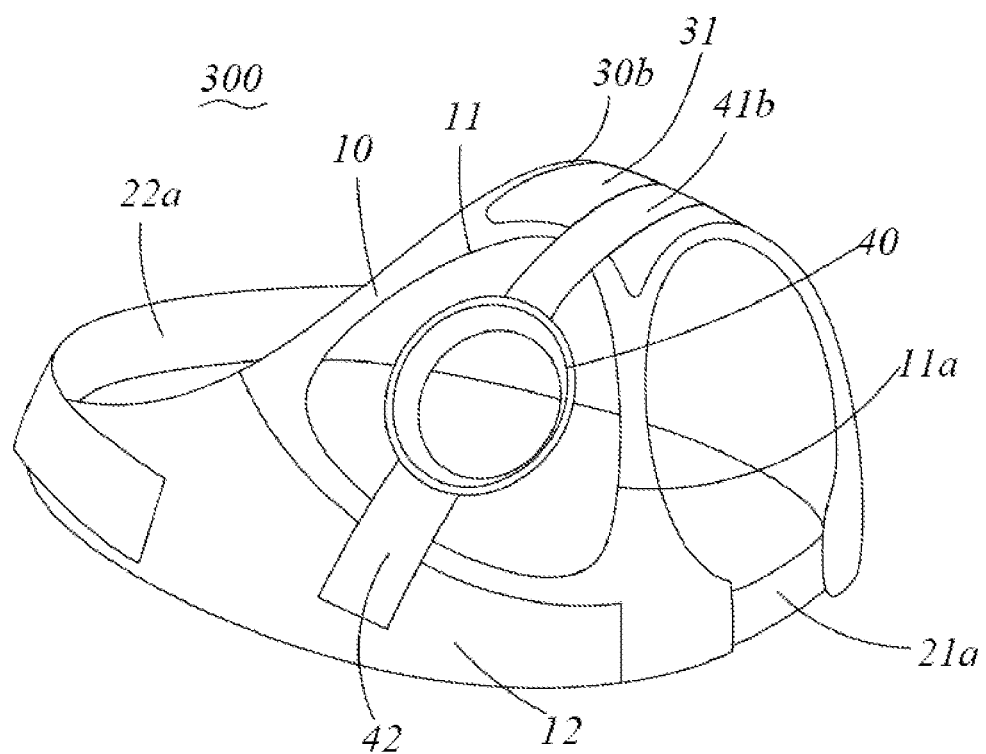
FIG. 5 is a perspective view of a fixing device of a wireless charger in a third preferred embodiment of the present invention.
Figure 6:
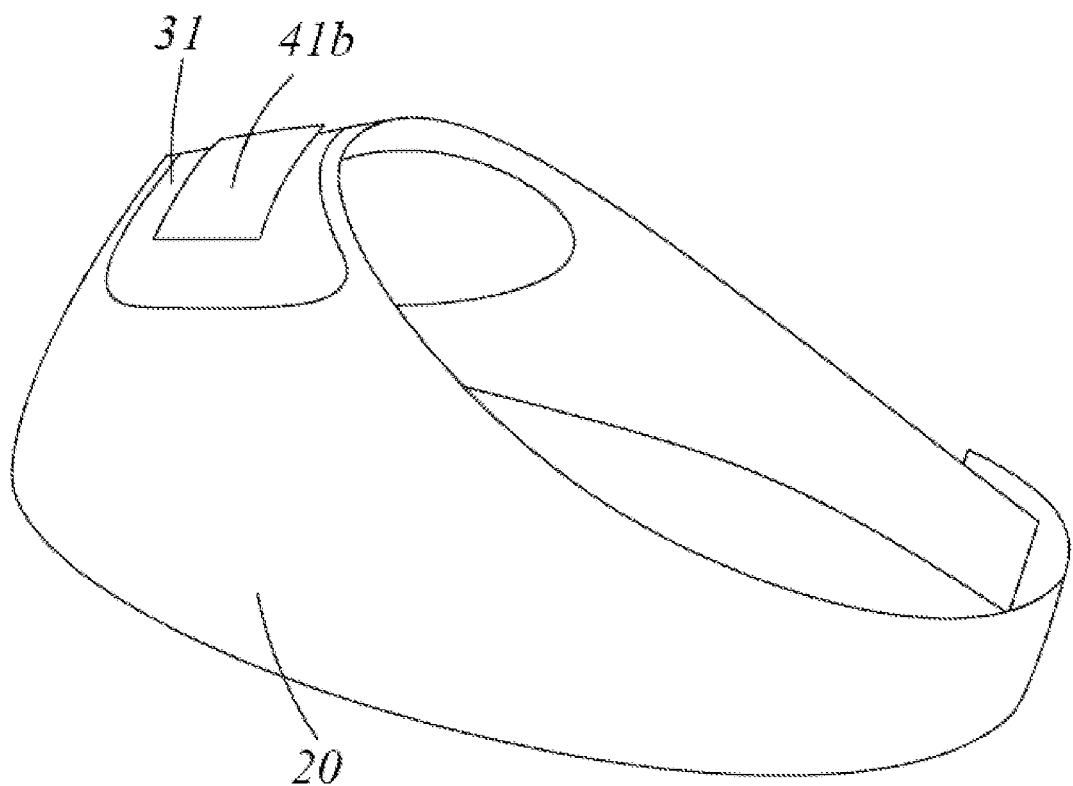
FIG. 6 is a perspective view of the fixing device of FIG. 5 as viewed from another aspect.

FIG. 5 and FIG. 6 show a third preferred embodiment of the fixing device of the wireless charger of the present invention. Components of the fixing device 300 of the wireless charger which are denoted with the same reference numbers as the second embodiment have the same structures and functions and will not be described in detail any more. Different from the second embodiment, the shoulder supporting portion 30*b* is also provided with the shoulder fluffy surface 31. Correspondingly, the positioning strap 41*b* is provided with the female hook-and-loop fastener belt. After the position of the charger fixing seat 40 is adjusted through the fixing strap 42, the positioning strap 41*b* is fixed relative to the position of the shoulder supporting portion 41*b* in a way that the female hook-and-loop fastener belt on the positioning strap 41*b* engages with the shoulder fluffy surface 31 on the shoulder supporting portion 30*b*, thereby preventing the displacement of the charger fixing seat 40 during use. Alternatively, the positioning strap 41*b* is fixed first, and then the fixing strap 42 is connected to the fluffy surface 12 of the front sheet 10.

Figure 7:
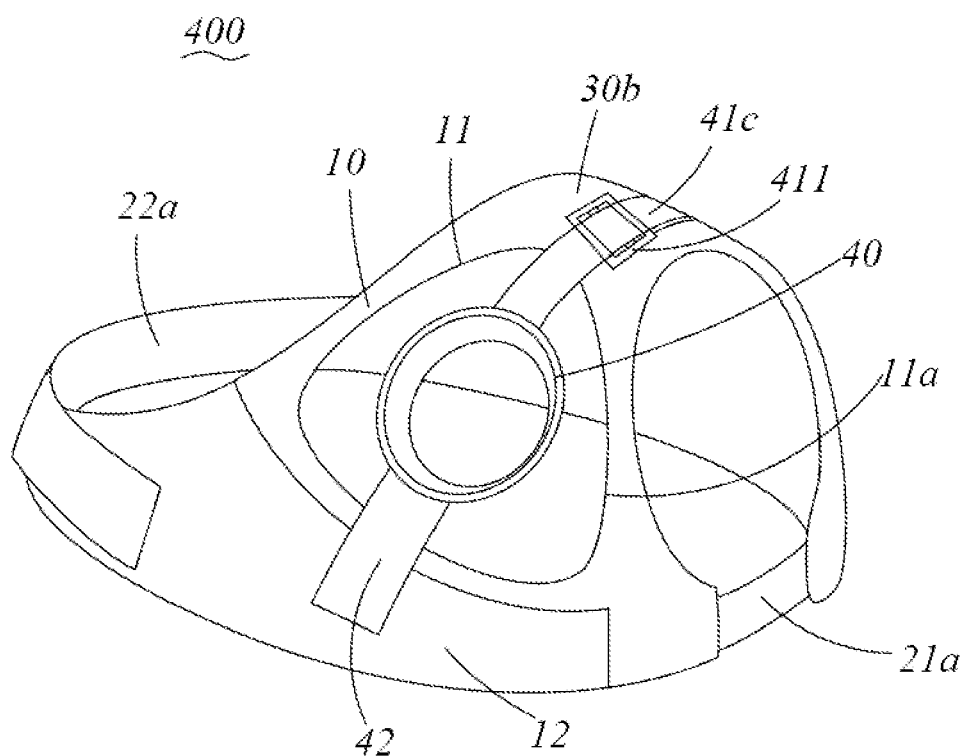
FIG. 7 is a perspective view of a fixing device of a wireless charger in a fourth preferred embodiment of the present invention.
Figure 8:
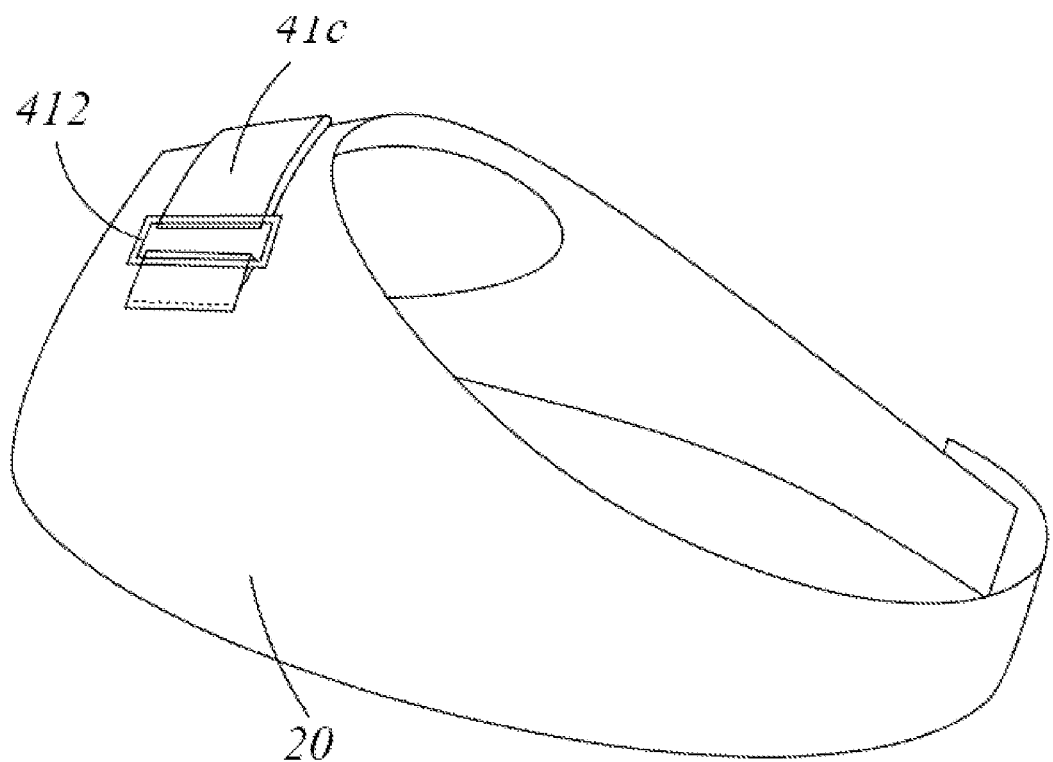
FIG. 8 is a perspective view of the fixing device of FIG. 7 as viewed from another aspect.

FIG. 7 and FIG. 8 show a fourth preferred embodiment of the fixing device of the wireless charger of the present invention. Components of the fixing device 400 of the wireless charger which are denoted with the same reference numbers as the second embodiment have the same structures and functions and will not be described in detail any more. Different from the second embodiment, the positioning strap 41*c* is configured adjustable in length. The positioning strap 41*c* is connected to a position of the rear sheet 20 adjacent to the shoulder fixing portion 30*b*. A fixing ring 412 is fixed on the shoulder fixing portion 30*b* or rear sheet 20. One end of the positioning strap 41*c* is connected to the fixing ring 412. An adjustable ring 411 is disposed on the positioning strap 41*c*. The length of the positioning strap 41*c* connected to the charger fixing seat 40 can be adjusted by operating the adjustable ring 411 and the positioning strap 41*c*. Hence, after the position of the charger fixing seat 40 is adjusted, the fixing strap 42 is connected to the fluffy surface 12 of the front sheet 10.

Figure 9:
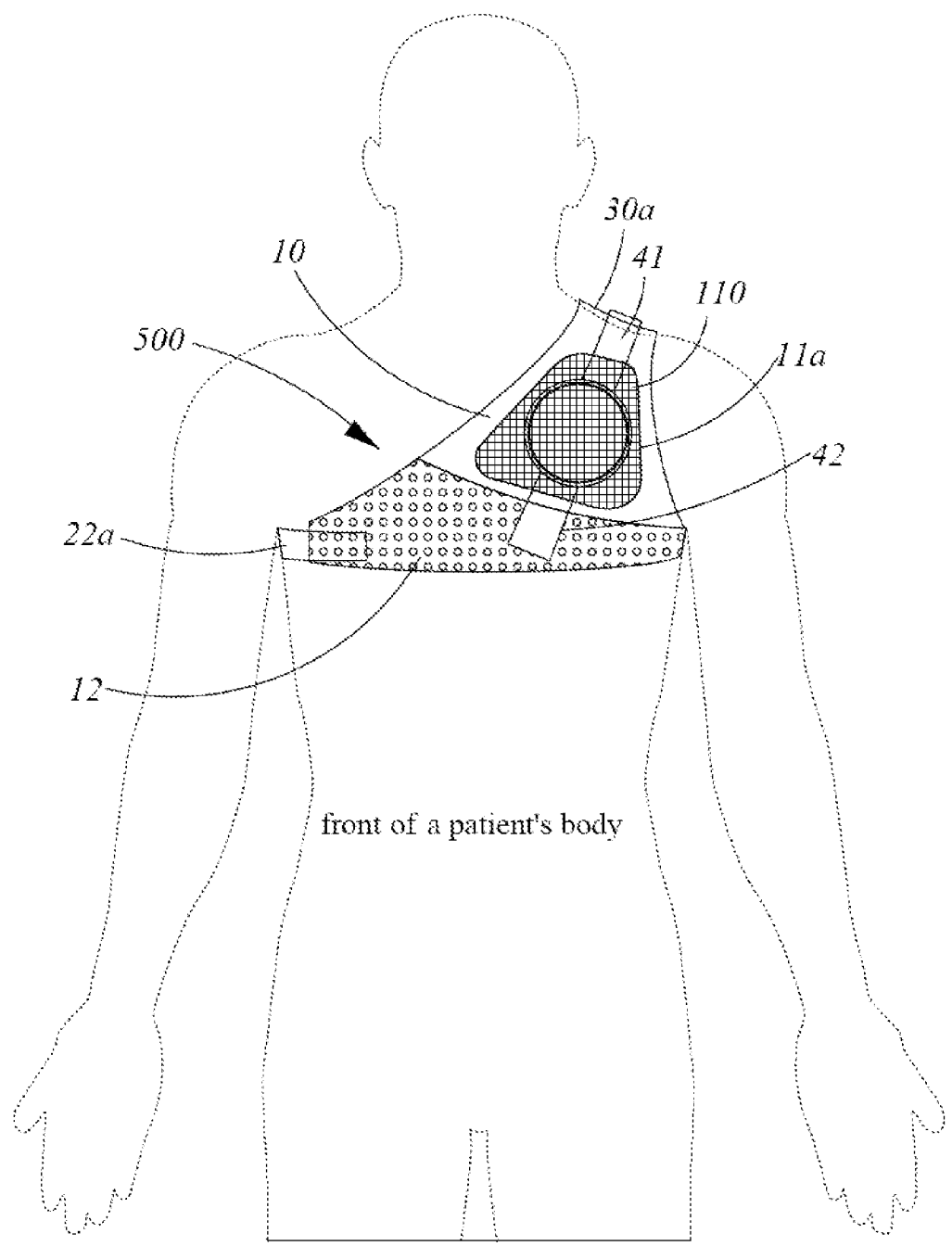
FIG. 9 is a front view when a fixing device of a wireless charger in a fifth preferred embodiment of the present invention is worn on a patient's body, wherein a shoulder supporting portion is located on the left side.
Figure 10:
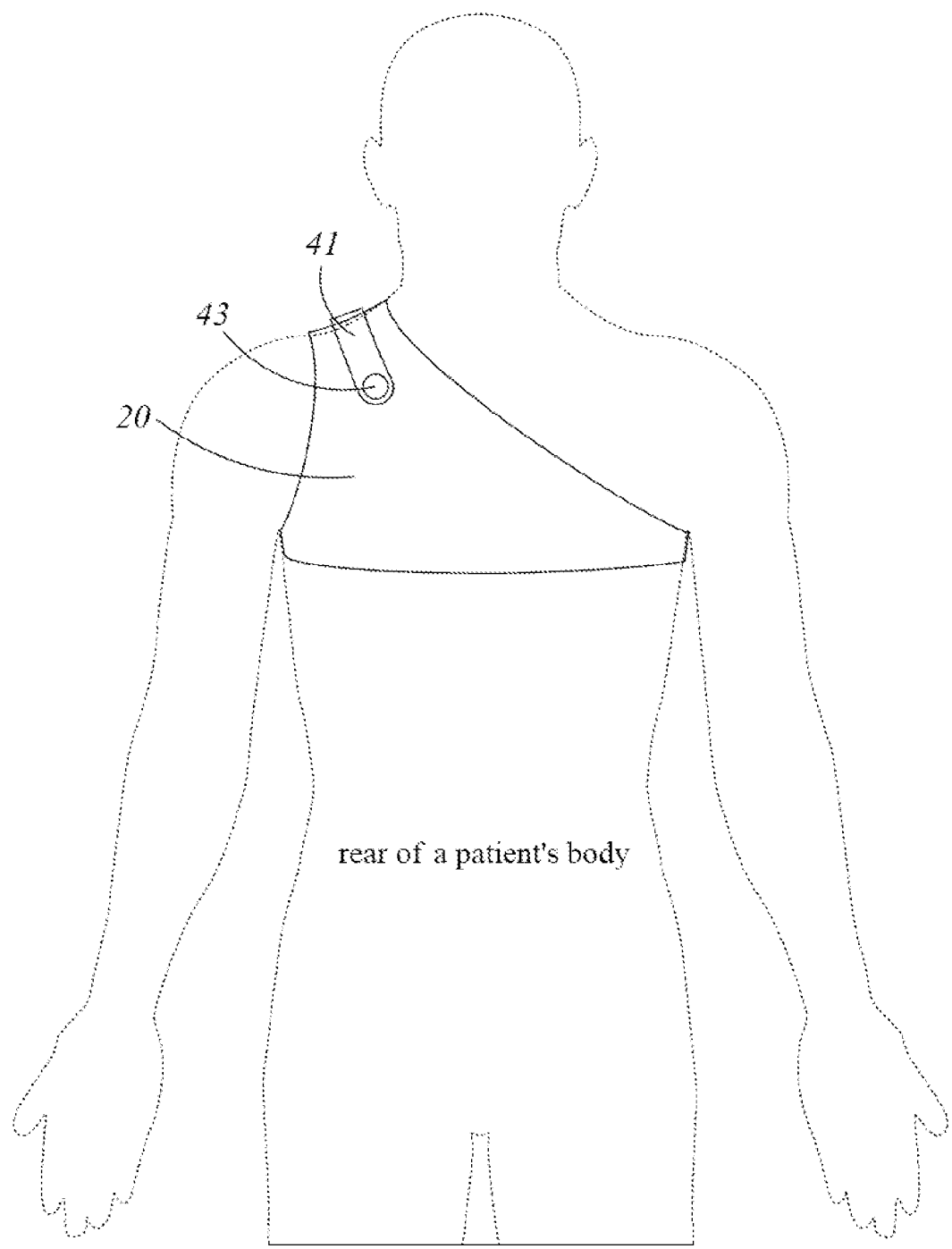
FIG. 10 is a rear view when the fixing device of FIG. 9 is worn on a patient's body.

FIG. 9 and FIG. 10 show a fifth preferred embodiment of the fixing device of the wireless charger of the present invention. Components of the fixing device 500 of the wireless charger which are denoted with the same reference numbers as the second embodiment have the same structures and functions and will not be described in detail any more. Different from the second embodiment, the charging opening 11*a* is filled with a mesh-like fabric to facilitate heat dissipation upon charging. The charging opening Ila may be disposed on the left side or right side relative to the patient's body.

Figure 11:
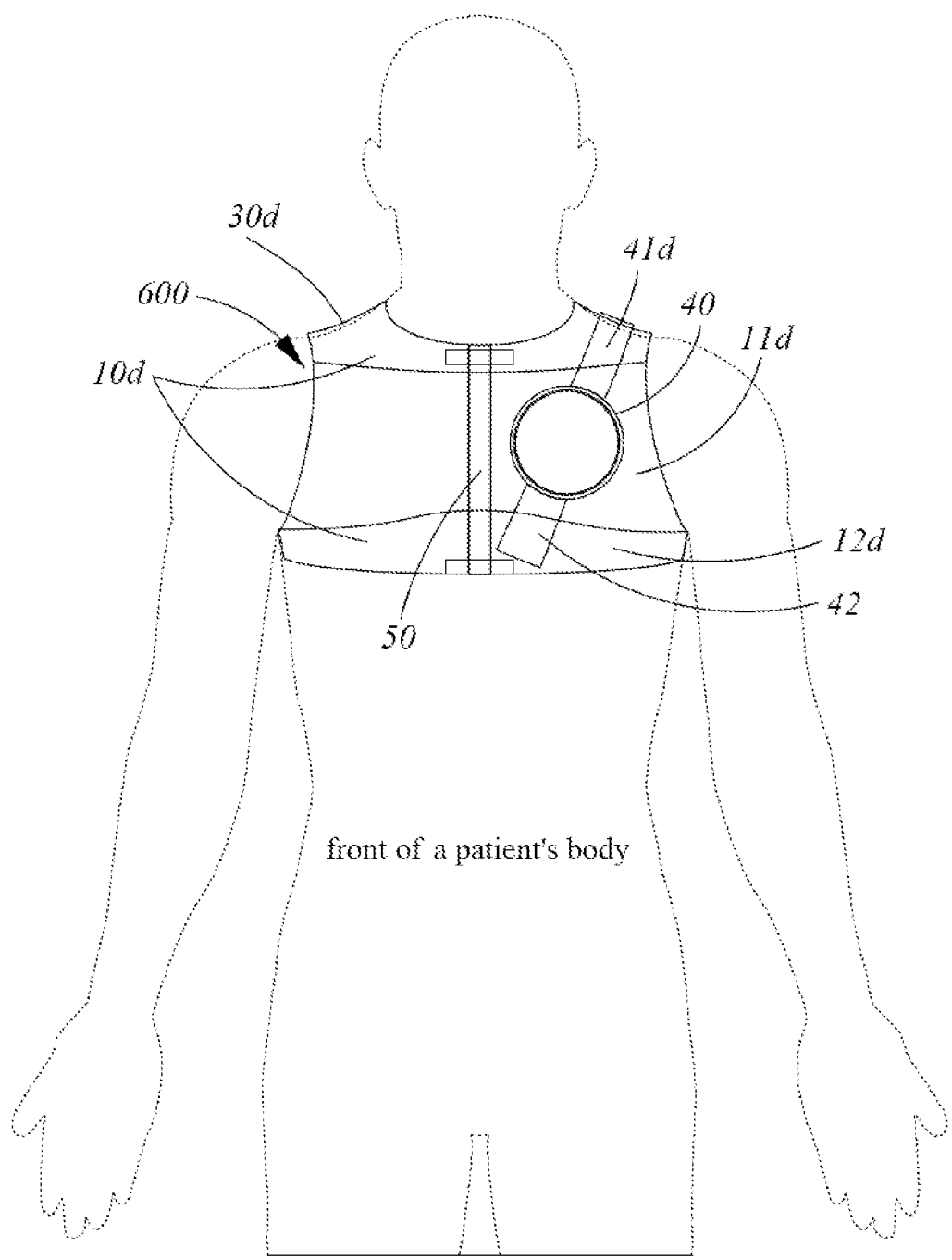
FIG. 11 is a front view when a fixing device of a wireless charger in a sixth preferred embodiment of the present invention is worn on a patient's body.
Figure 12:
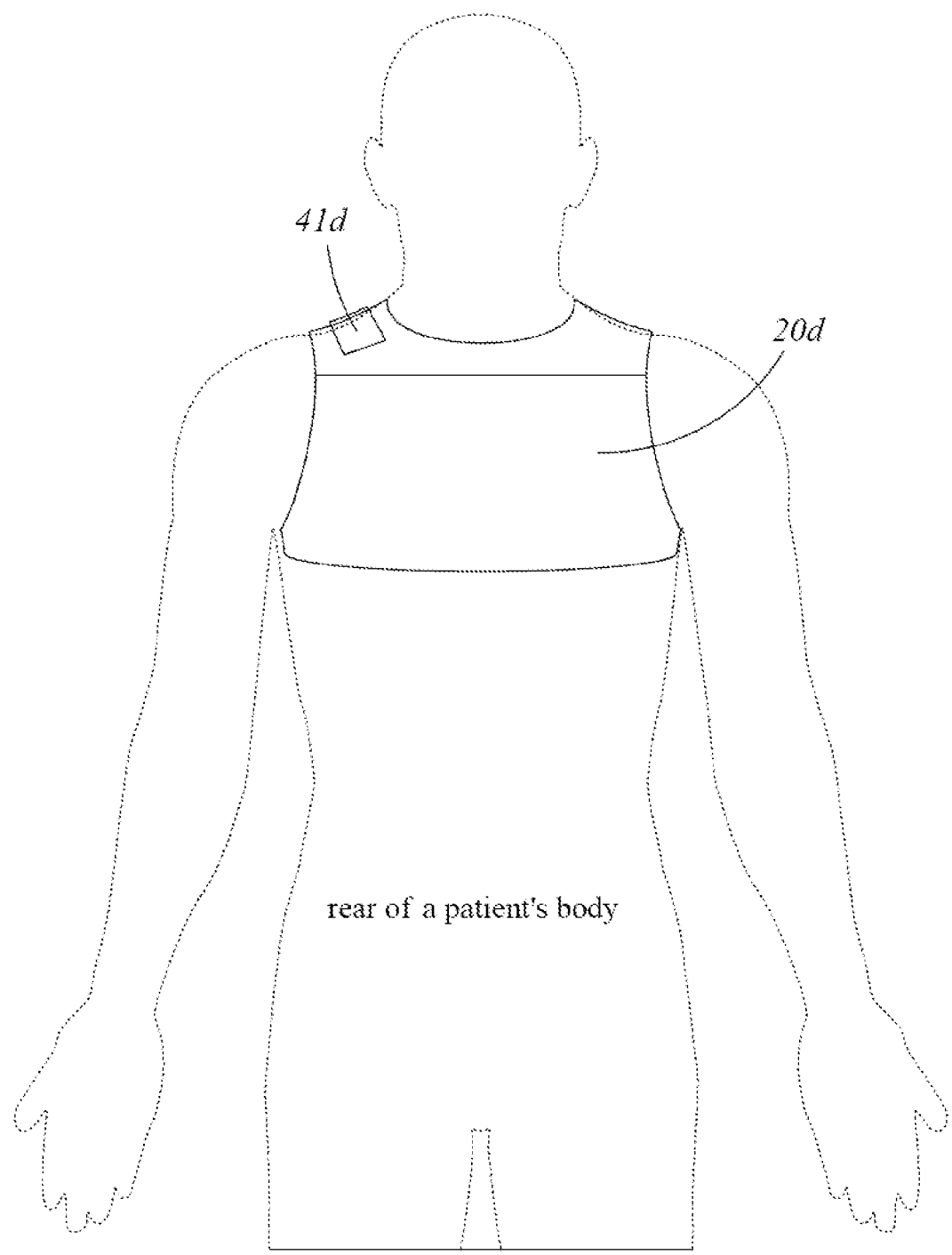
FIG. 12 is a rear view when the fixing device of FIG. 11 is worn on a patient's body.

FIG. 11 and FIG. 12 show a sixth preferred embodiment of the fixing device of the wireless charger according to the present invention. The fixing device 600 of the wireless charger comprises a supporting member wearable on a patient's body and having a vest structure. The supporting member comprises a shoulder supporting portion 30*d*, and a front sheet 10*d* and a rear sheet 20*d* respectively connected to the front and rear of the shoulder supporting portion 30*d*. Bottom sides of the front sheet 10*d* and the rear sheet 20*d* are connected via a left connecting portion and a right connecting portion. The left connecting portion and the right connecting portion are used to form a shoulder cuff to be supported under the patient's armpit. The fixing device of the wireless charger further comprises an adjustment strap provided with a charger fixing seat 40. One end of the adjustment strap is connected to the shoulder supporting portion 30*d* or the rear sheet 20*d* of the shoulder supporting member. The front sheet 10*d* is provided with a charging opening 11*d*. The other end of the adjustment strap operably brings the charger fixing seat 40 to be adjusted to a position in the charging opening 11*d* corresponding to the implantable medical device, and is separably connected to the front sheet 10 of the shoulder supporting member.

In the present embodiment, the supporting member is entirely configured as a dual-shoulder vest structure, i.e., two shoulder supporting portions 30*d* are provided with one on each of the left side and right side. The charging opening 11*d* may also be arranged along both the left and right sides, e.g., the supporting member is entirely configured a left-right symmetrical structure. The shoulder supporting portion 30*d* and the front sheet 10*d* and rear sheet 20*d* are directly connected together, and preferably the shoulder supporting portion 30*d* and the front sheet 10*d* and rear sheet 20*d* are an integral structure. Furthermore, the left and right connecting portions may also be directly connected to the front sheet 10*d* and rear sheet 20*d*. The front sheet 10*d* is configured as a two-half structure from both sides. A slide fastener structure 50 is disposed between the both sides. The put-on and put-off of the supporting member can be achieved by operating the slide fastener structure 50. The front sheet 10*d* comprises an upper portion and a lower portion spaced apart, i.e., the charging opening 11*d* spaces the upper portion of the front sheet 10*d* from the lower portion of the front sheet 10*d*. The fluffy surface is disposed on the lower portion of the front sheet 10*d*. The positioning strap 41*d* may also be configured as an elastic band whose one end is fixed to the shoulder supporting portion 30*d* or rear sheet 20*d*. The configuration of the fixing strap 42 and the connection manner with the front sheet 10*d* may be the same as the previous embodiments and will not be detailed any more here.

Figure 13:
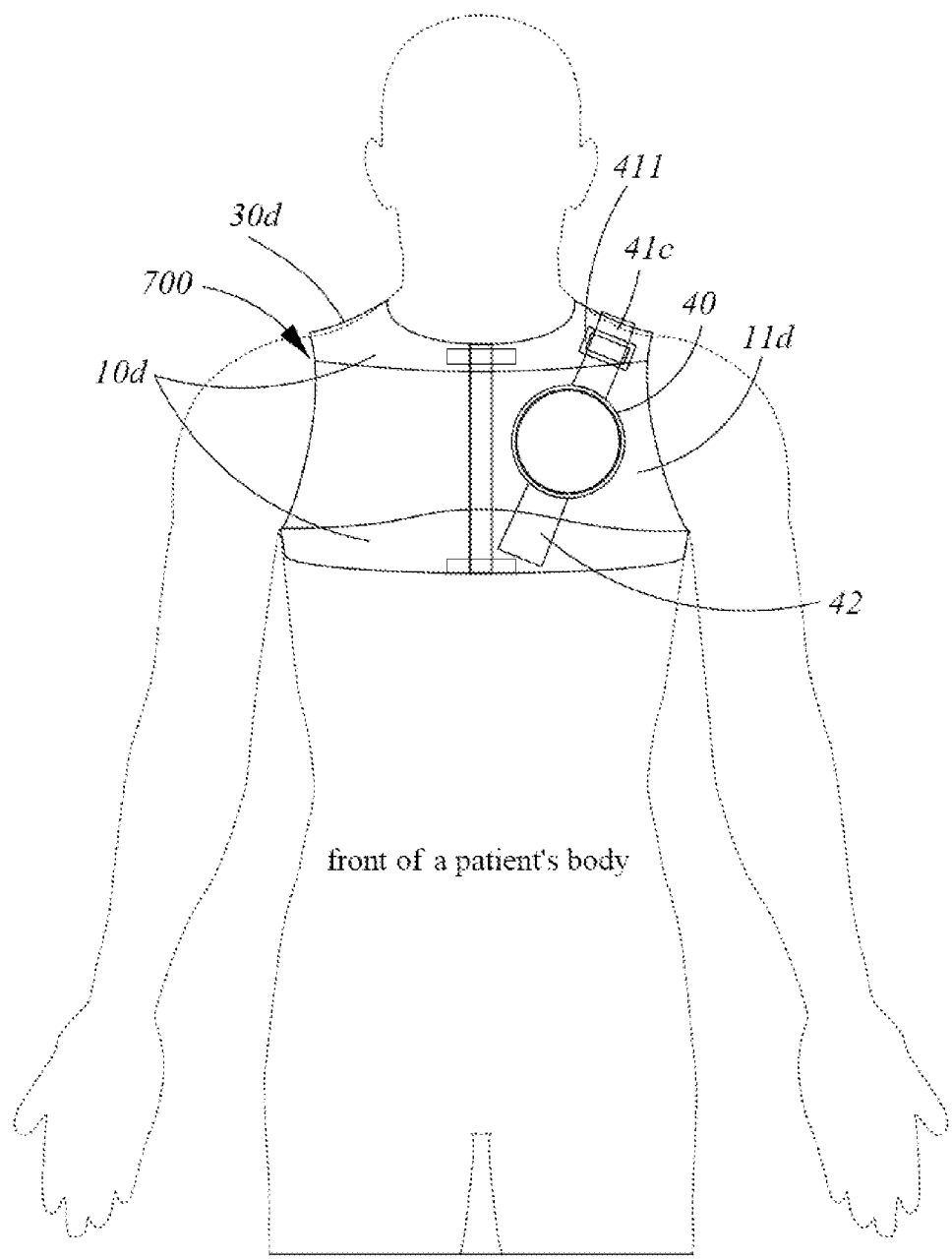
FIG. 13 is a front view when a fixing device of a wireless charger in a seventh preferred embodiment of the present invention is worn on a patient's body.
Figure 14:
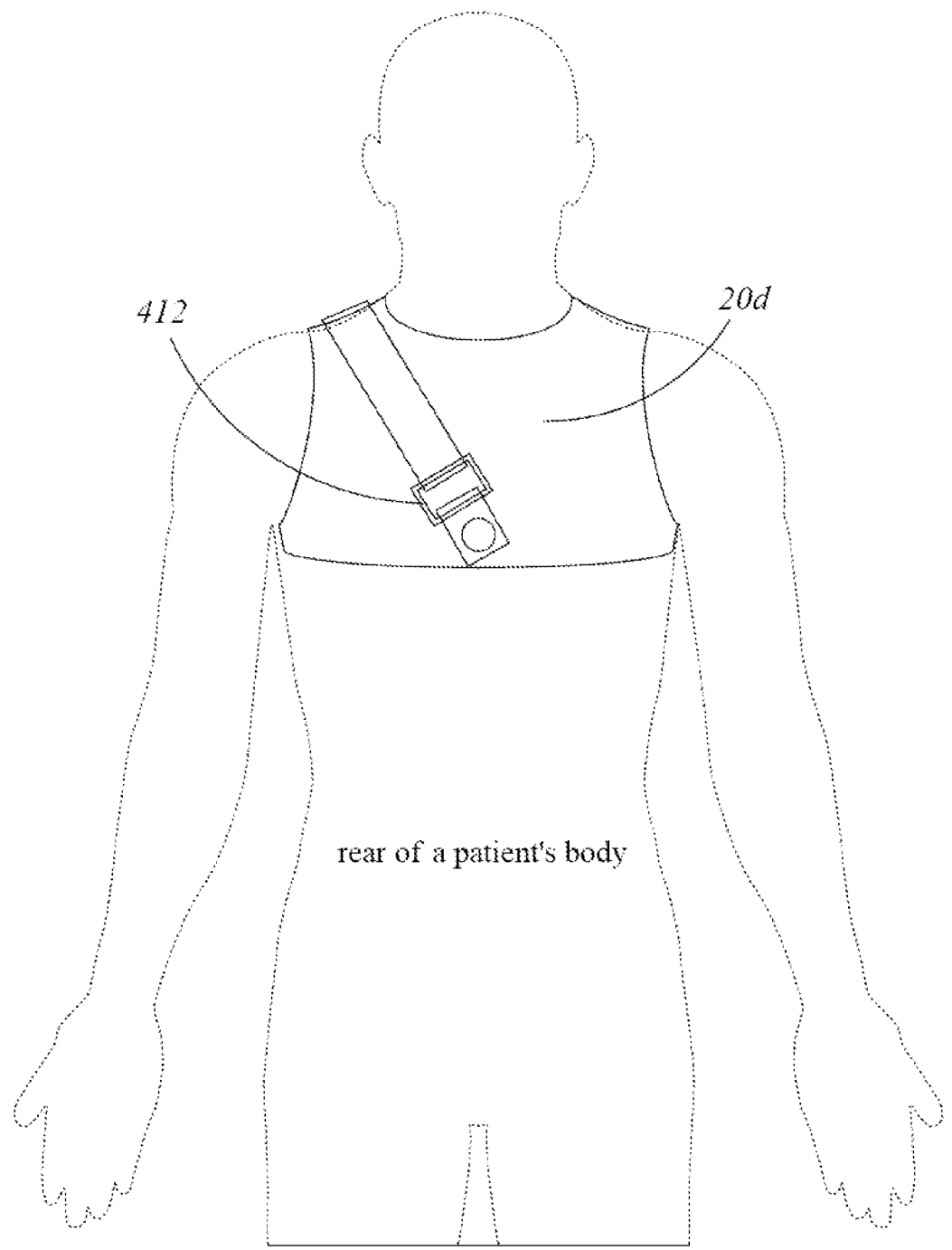
FIG. 14 is a rear view when the fixing device of FIG. 13 is worn on a patient's body.
Figure 15:
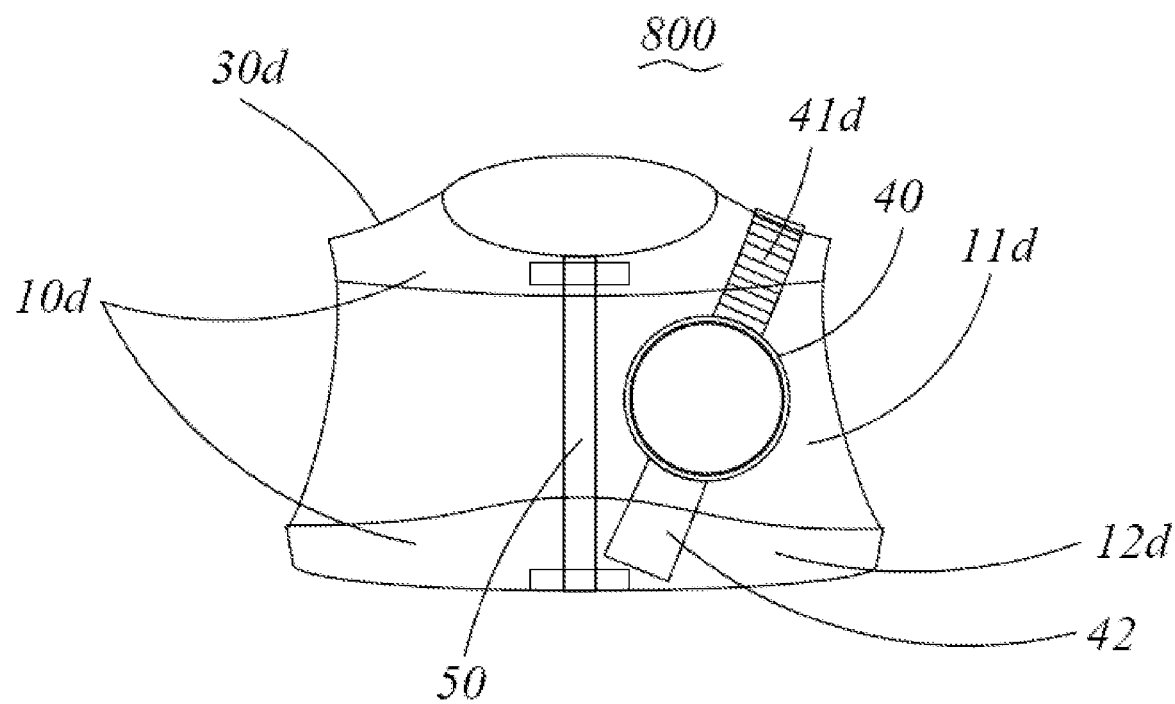
FIG. 15 is a front view of a fixing device of a wireless charger in an eighth preferred embodiment of the present invention.
Figure 16:
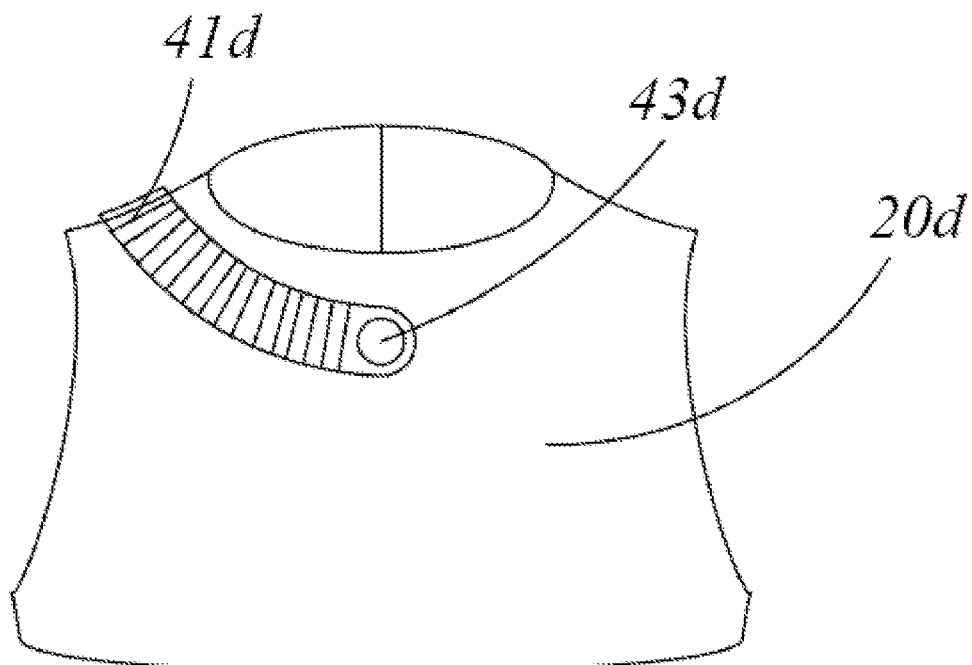
FIG. 16 is a rear view of the fixing device of FIG. 15.
Figure 17:
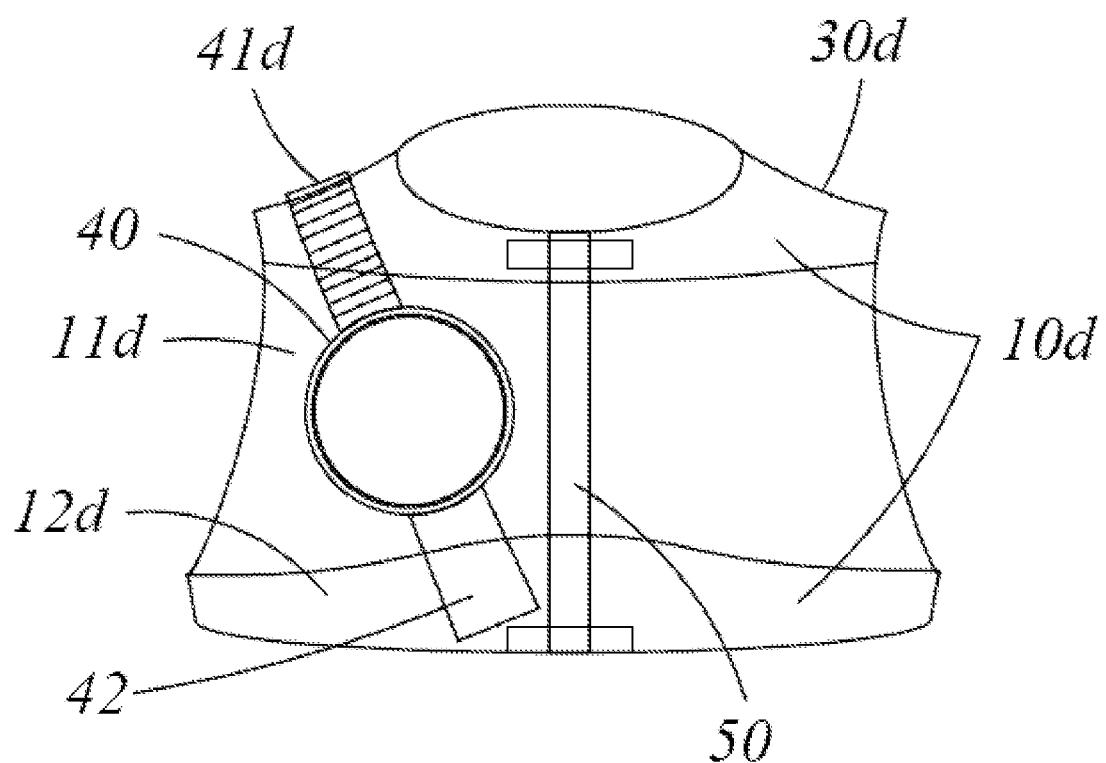
FIG. 17 is a front view of the fixing device of FIG. 15 in another use state.
Figure 18:
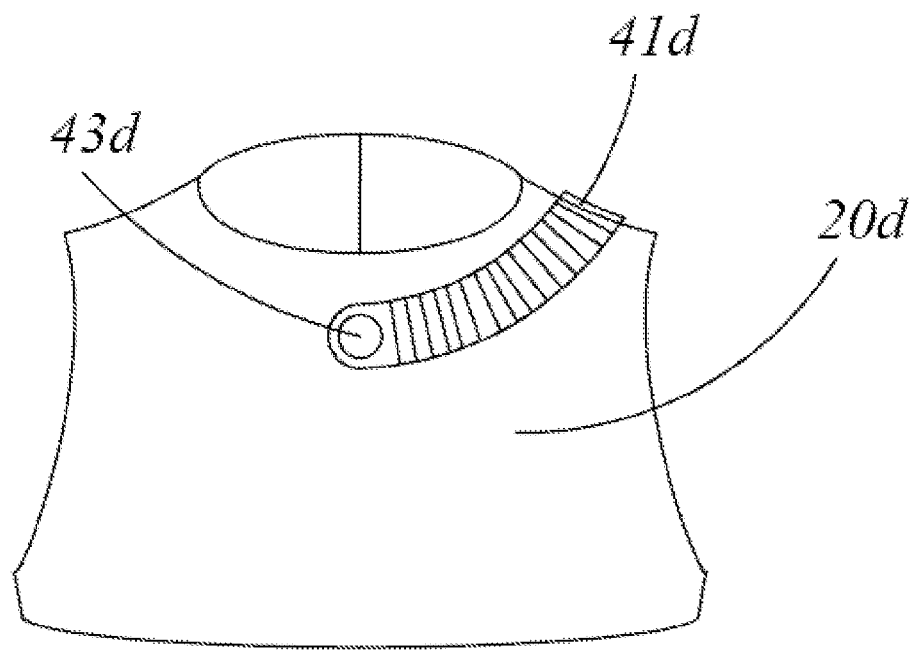
FIG. 18 is a rear view of the fixing device of FIG. 17.
Figure 19:
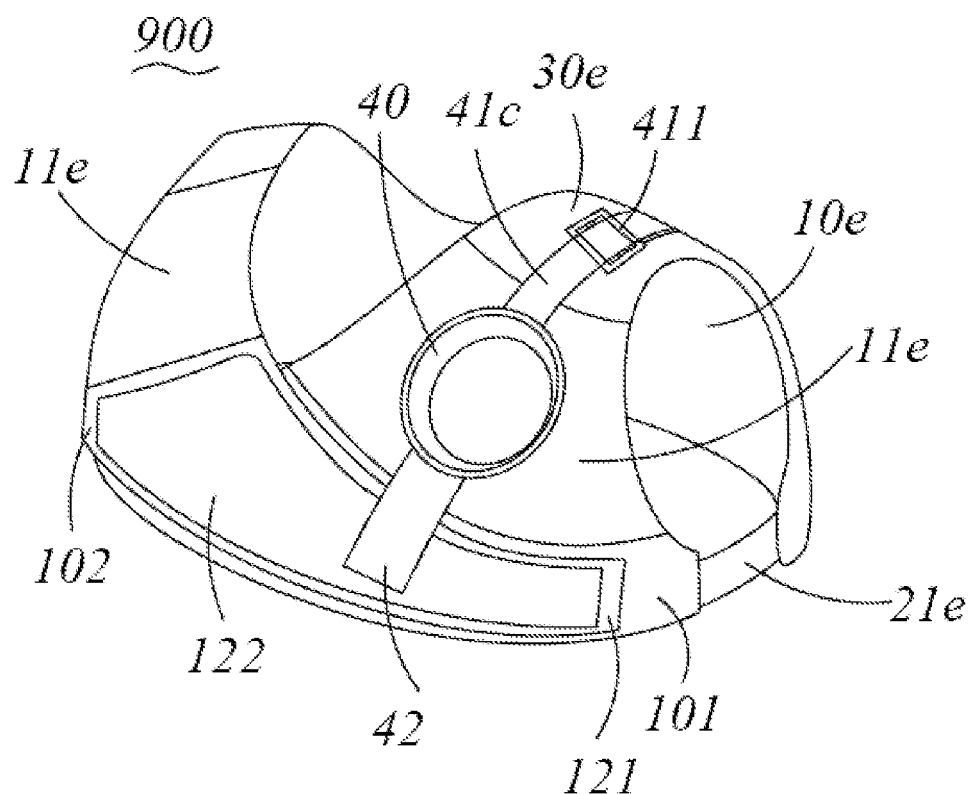
FIG. 19 is a perspective view of a fixing device of a wireless charger in a ninth preferred embodiment of the present invention.
Figure 20:
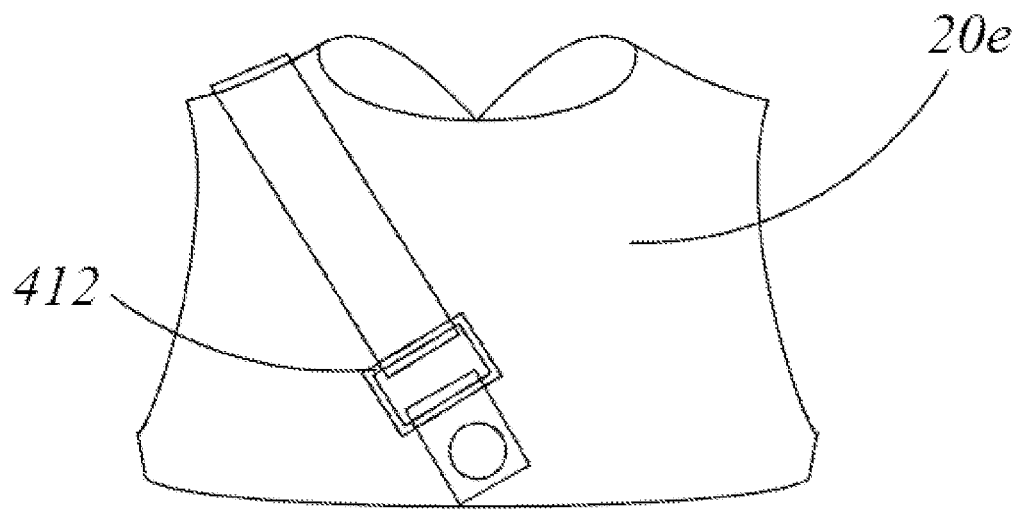
FIG. 20 is a rear view of the fixing device of FIG. 19.
Figure 21:
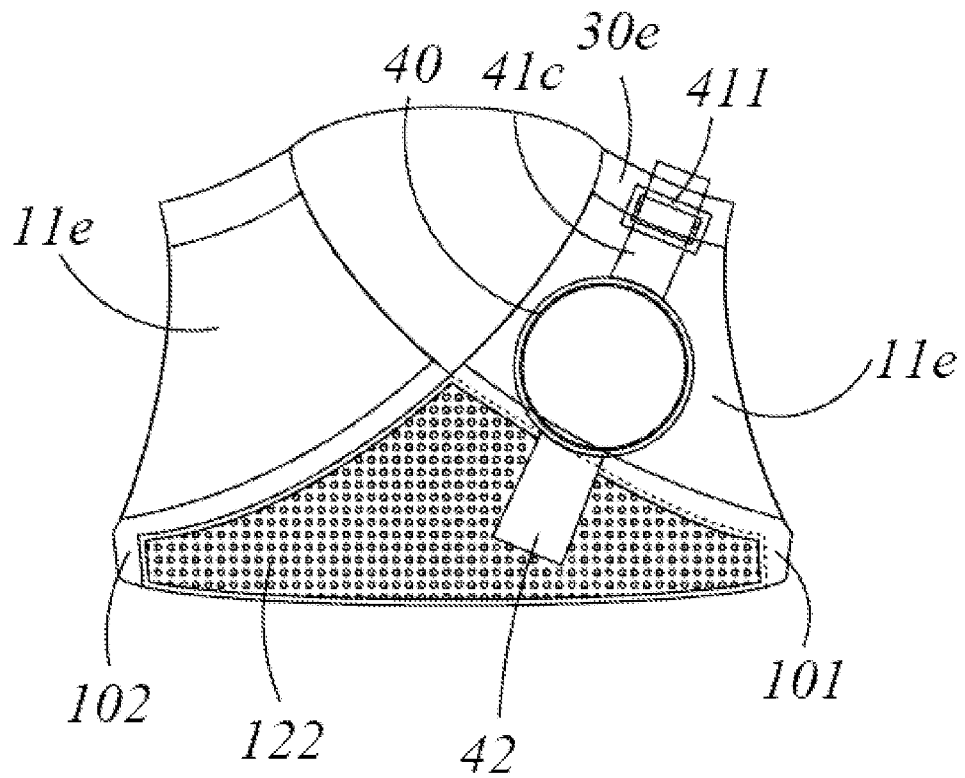
FIG. 21 is a front view of the fixing device of FIG. 19.
Figure 22:
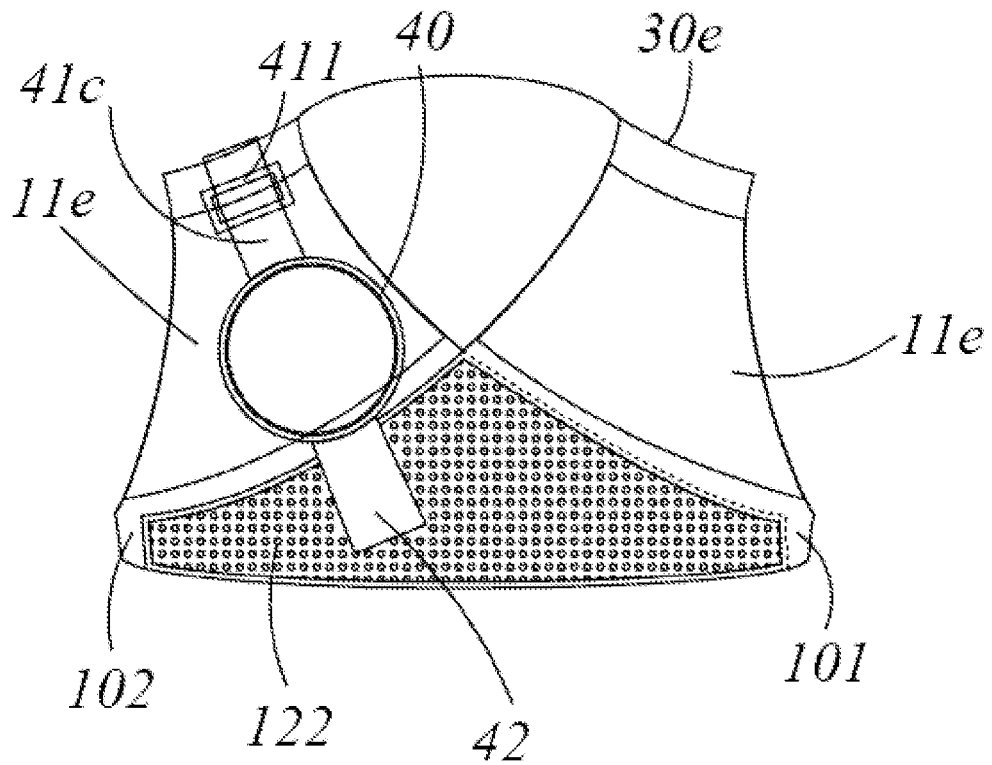
FIG. 22 is a front view of the fixing device of FIG. 19 in another use state.
Figure 23:
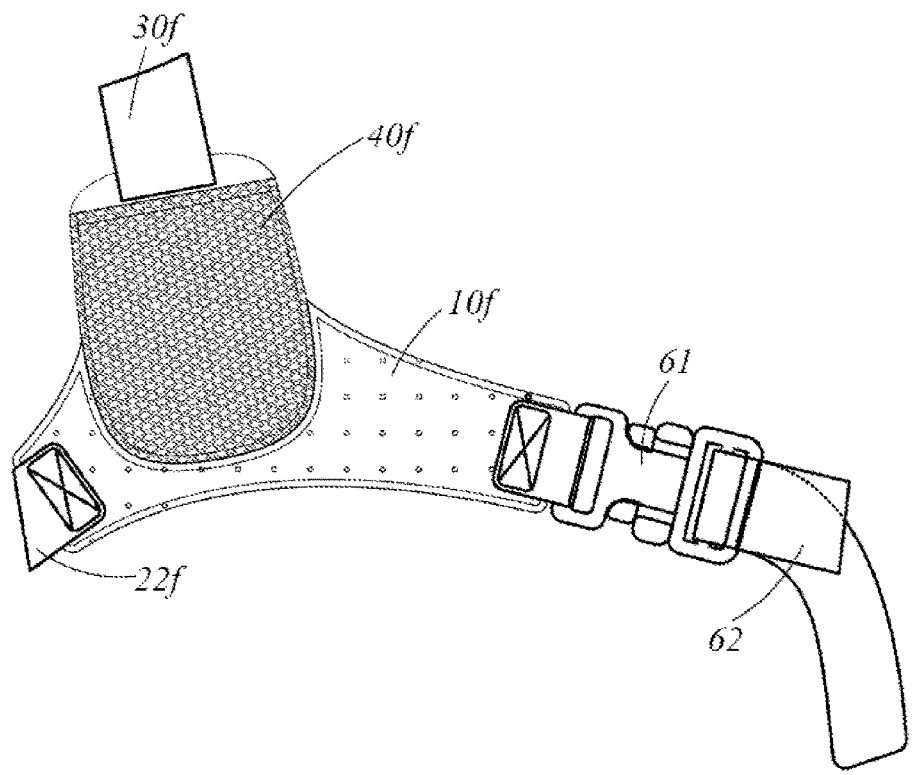
FIG. 23 is a perspective view of a fixing device of a wireless charger in a tenth preferred embodiment of the present invention.

FIG. 13 and FIG. 14 show a seventh preferred embodiment of the fixing device of the wireless charger according to the present invention. Components of the fixing device 700 of the wireless charger which are denoted with the same reference numbers as the sixth embodiment have the same structures and functions and will not be described in detail any more. Different from the sixth embodiment, the positioning strap 41*c* is configured the same as the fourth embodiment and is adjustable in length. The shoulder fixing portion 30*d* or rear sheet 20*d* is fixed with a fixing ring 412. One end of the positioning strap 41*c* is connected to the fixing ring 412. The positioning strap 41*c* is provided with an adjusting ring 411. The length of the positioning strap 41*c* connected to the charger fixing seat 40 can be adjusted by operating the adjustment ring 411 and the positioning strap 41*c*. The adjustment ring 411 may be considered as a length adjuster, and it moves in a lengthwise direction of the positioning strap 41*c* to adjust the distance between a connection end of the positioning strap 41*c* connected to the supporting member and the charger fixing seat 40. Hence, after the position of the charger fixing seat 40 is adjusted, the fixing strap 42 is connected to the front sheet 10. The fixing ring 412 may be connected to the lower side of the rear sheet 20*d* via the fixing snap.

FIG. 15 through FIG. 18 show an eighth preferred embodiment of the fixing device of the wireless charger according to the present invention. Components of the fixing device 800 of the wireless charger which are denoted with the same reference numbers as the sixth embodiment have the same structures and functions and will not be described in detail any more. Different from the sixth embodiment, the positioning strap 41*d* is configured as a strap of an extensible material, and its one end connected to the rear sheet 20*d* is connected to the rear sheet 20*d* via a fixing snap 43*d*. The fixing snap 43*d* is disposed in the middle of the rear sheet 20d. Hence, the positioning strap 41d may selectively bypass from the left shoulder or right shoulder so that the charger fixing seat can be conveniently adjusted to the left side or right side of the patient's body.

FIG. 19 through FIG. 22 show a ninth preferred embodiment of the fixing device of the wireless charger according to the present invention. The fixing 900 of the wireless charger comprises a supporting member wearable on a patient's body and having a vest structure. The supporting member comprises a shoulder supporting portion 30e, and a front sheet and a front sheet 20e respectively connected to the front and rear of the shoulder supporting portion 30e. Bottom sides of the front sheet and the rear sheet 20e are connected via a left connecting portion 21e and a right connecting portion. The left connecting portion 21e and the right connecting portion are used to form a shoulder cuff to be supported under the patient's armpit. The fixing device of the wireless charger further comprises an adjustment strap provided with a charger fixing seat 40. The configuration of the adjustment strap is similar to that of the sixth embodiment and will not be detailed any more here.

In the present embodiment, the supporting member is entirely configured as a dual-shoulder vest structure, i.e., two shoulder supporting portions 30e are provided with one on each of the left side and right side. The charging opening 11e may also be arranged along both the left and right sides, e.g., the supporting member is entirely configured a left-right symmetrical structure. The front sheet comprises a left front sheet 101 and a right front sheet 102 which are partially overlappable from left to right. The shoulder supporting portion 30d and the front sheet 10d and rear sheet 20d are directly connected together, and preferably the shoulder supporting portion 30e and the left front sheet 101 and right front sheet 102 and rear sheet 10e are an integral structure. The left connecting portion 21e and right connecting portion may be configured as an extensible belt connecting the left front sheet 101 with the rear sheet 10e and an extensible belt connecting the right front sheet 102 with the rear sheet 10e, respectively. The left front sheet 101 is provided with a first male hook-and-loop fastener belt having a fluffy surface 121. An outer side of the right front sheet 102 is provided with a second male hook-and-loop fastener belt having a fluffy surface 122. An inner side of the right front sheet 102 is provided with a third female hook-and-loop fastener belt engaging with the fluffy surface 121. The left front sheet 101 and right front sheet 102 achieve detachable connection of the two via the engagement of the third female hook-and-loop fastener belt and the fluffy surface 121 so that the size of the supporting member may be adjusted according to the patient's body. The fixing strap 42 may also be connected to the fluffy surface 122 of the right front sheet 102 via the female hook-and-loop fastener belt to achieve affixation of the charger fixing seat 40 relative to the supporting member. Certainly, the left-right overlappable manner of the left front sheet 101 and right front sheet 102 are interchangeable. Furthermore, the charger fixing seat 40 may be fixed in the charging opening on the left side or in the charging opening on the right side via the positioning strap 41c and fixing strap 42.

FIG. 23 through FIG. 27 show a tenth preferred embodiment of the fixing device of the wireless charger according to the present invention. The fixing device 1000 of the wireless charger comprises a supporting member wearable on a patient's body and an adjustment structure connected to the supporting member. A charger fixing seat 40f is connected to one of the supporting member and the adjustment structure. The adjustment structure comprises an adjustment strap 62 and a fixing buckle 61 engaging with the adjustment strap 62, one end of the adjustment strap 62 is connected to the supporting member, the other end of the adjustment strap 62 operably brings the supporting member or the charger fixing seat to be adjusted to a position where the charger fixing seat corresponds to the implantable medical device, and the position where the adjustment strap 62 engages with the fixing buckle 61 is fixed relative to the supporting member.

In the present embodiment, preferably, the charger fixing seat 40f is connected to the supporting member, one end of the fixing buckle 61 is connected to the supporting member, and the other end of the fixing buckle 61 is movably connected to the adjustment strap 62. The fixing buckle 61 comprises a male snap and a female snap which are detachably connected. The male snap and female snap are respectively connected to the supporting member and the adjustment strap 61. In other words, the patient may conveniently put on or put off the fixing device by opening the fixing buckle 61. The fixing buckle 61 may be configured as a plug-in buckle, a male buckle or a female buckle of the plug-in buckle is connected to the adjustment ring. The other end of the adjustment strap 62 passes through the adjustment ring and is configured as a free end. The position of the supporting member may be adjusted by pulling of the free end of the adjustment strap 62, and the fixing buckle 61 will bring the supporting member to move, until the charger fixing seat 40f corresponds to the position of the implantable medical device. Locking is achieved by releasing the adjustment strap 62, i.e., the engagement position of the adjustment strap 62 and the fixing buckle 61 is fixed relative to the supporting member.

Furthermore, the supporting member comprises a supporting portion 30f, and a front sheet 10f and a rear sheet 20f connected to the front and rear of the shoulder supporting portion 30f, respectively. Bottom sides of the front sheet 10f and the rear sheet 20f are connected via a left connecting portion and a right connecting portion. The shoulder supporting portion, the front sheet and rear sheet here are also regarded as the shoulder of the supporting member, the front of the supporting member and the rear of the supporting member. The left connecting portion and the right connecting portion are used to form a shoulder cuff to be supported under the patient's armpit. In the present embodiment, an example is taken in which the right connecting portion 22f forms the shoulder cuff, and the left connecting portion is configured as the adjustment structure. One end of the adjustment strap 62 is connected to the rear sheet 20f, and the fixing buckle 61 is connected between the front sheet 10f and the adjustment strap 62. As such, the position of the charger fixing seat 40f is adjusted via the left connecting portion serving as the adjustment structure, so that the structure of the whole fixing device is simpler, the costs are lower and the use is more convenient.

Preferably, the shoulder supporting portion 30f and the right connecting portion 22f are both configured as elastic extensible belts to facilitate adaptation to patients with different body shapes and facilitate the patients to adjust the position of the charger fixing seat 40f. Certainly, other structures with the length adjustable may also be employed. The charger fixing seat 40f is configured as a storage bag. The storage bag is connected between the shoulder supporting portion 30f and the front sheet 10f to facilitate receiving the wireless charger. The storage bag comprises an outer bag 401 located outside and an inner bag 403 located inside. A partition layer 402 is disposed between the outer bag 401 and inner bag 403. The shoulder supporting portion 30f is connected to the partition layer 402. As such, the storage bag is disposed both inside and outside the supporting member to achieve wearing of the fixing device from inside and from outside so that the charger fixing seat 40f is fixed to the left chest and right chest. Certainly, it is also possible that the storage bag comprises an outer bag located outside and an inner bag located inside. The inner bag and outer bag are communicated with each other, that is, the storage bag is communicated from outside and inside without a partition layer being disposed. More materials are saved with one storage bag which may receive the wireless charger from both inside and outside. The storage bag may be made of a mesh-like fabric.

To facilitate fixing the wireless charger in the storage bag, a female hook-and-loop fastener belt is disposed on one of an outer side of the storage bag and an inner side of the storage bag, a male hook-and-loop fastener belt having a fluffy surface is disposed on the other of the outer side of the storage bag and inner side of the storage bag, and the female hook-and-loop fastener belt separably engages with the male hook-and-loop fastener belt to close at least one portion of the bag mouth of the storage bag. It is also possible that one of the outer side of the storage bag and the shoulder supporting portion 30f is provided with a female hook-and-loop fastener belt, the other of the outer side of the storage bag and the shoulder supporting portion 30f is provided with a male hook-and-loop fastener belt having a fluffy surface, and the female hook-and-loop fastener belt separably engages with the male hook-and-loop fastener belt to close at least one portion of the bag mouth of the storage bag.

Figure 24:
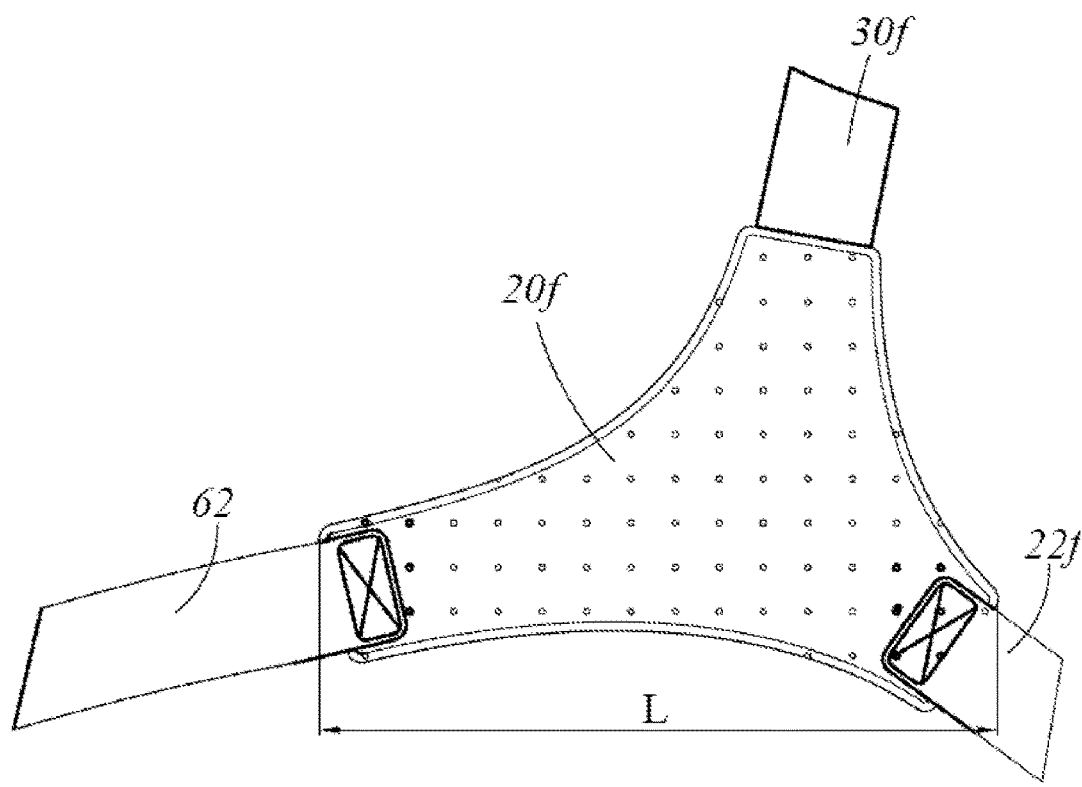
FIG. 24 is a rear view of the fixing device of FIG. 23.
Figure 25:
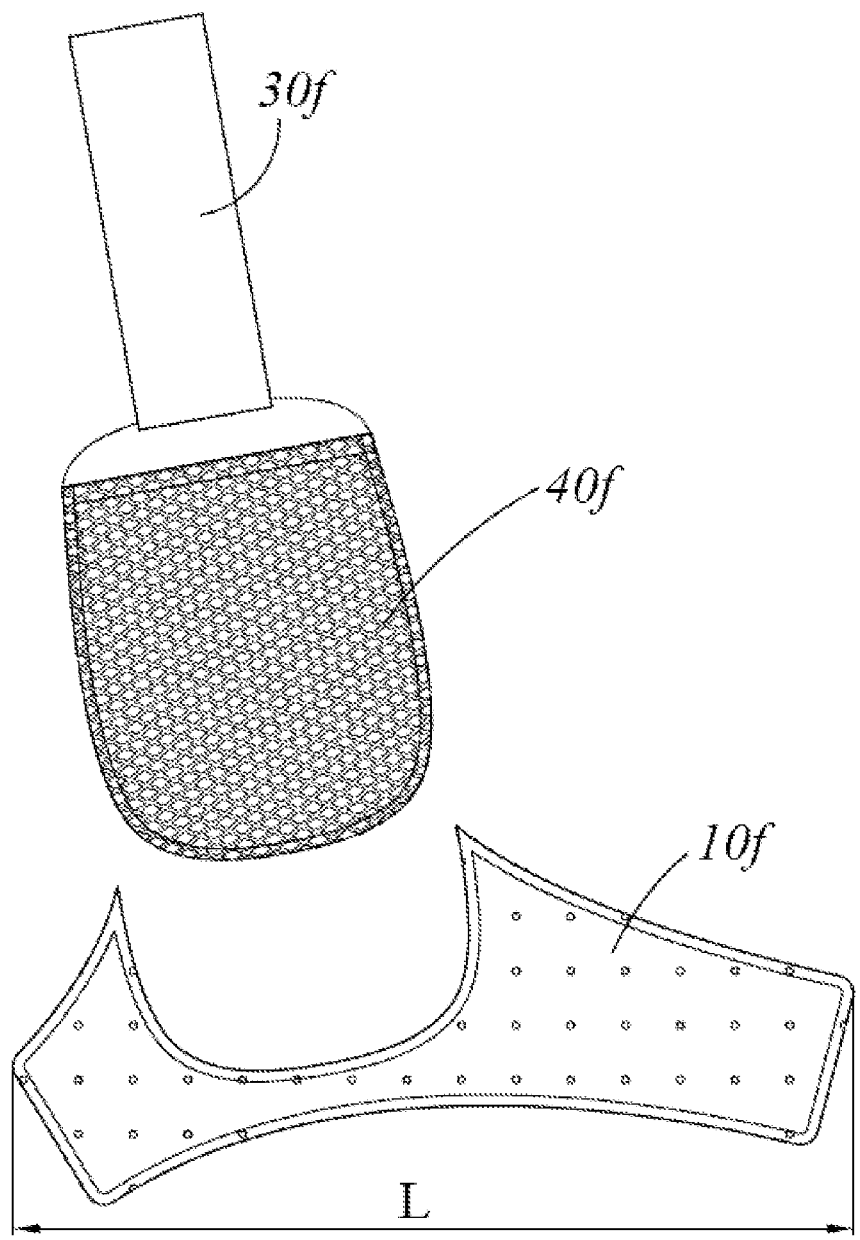
FIG. 25 is an exploded view of a charger fixing seat and a front sheet of the fixing device of FIG. 23.
Figure 26:
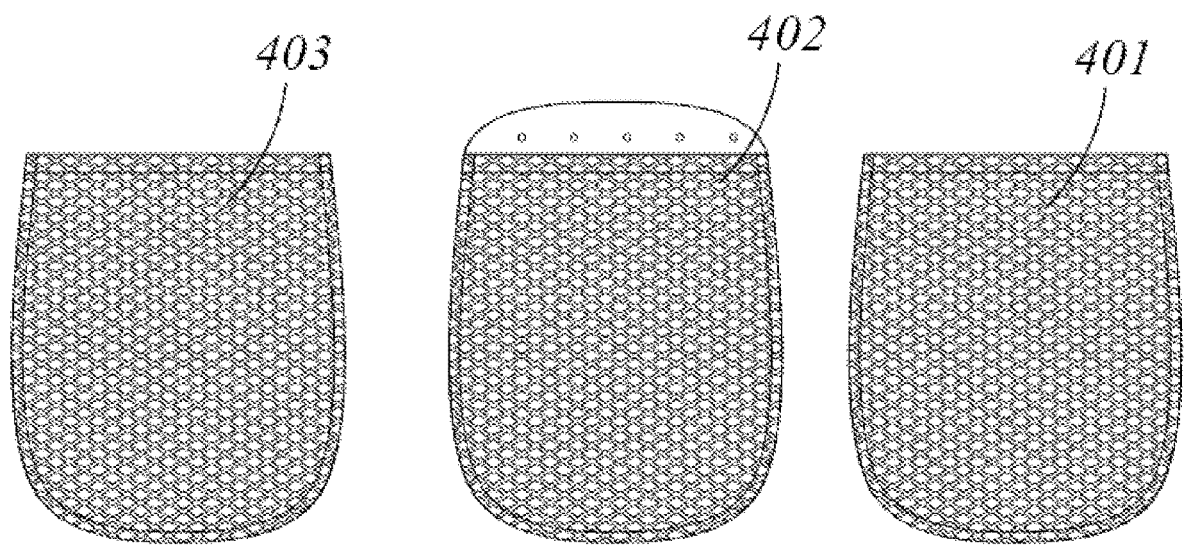
FIG. 26 is an exploded view of the charger fixing seat of the fixing device of FIG. 23.
Figure 27:
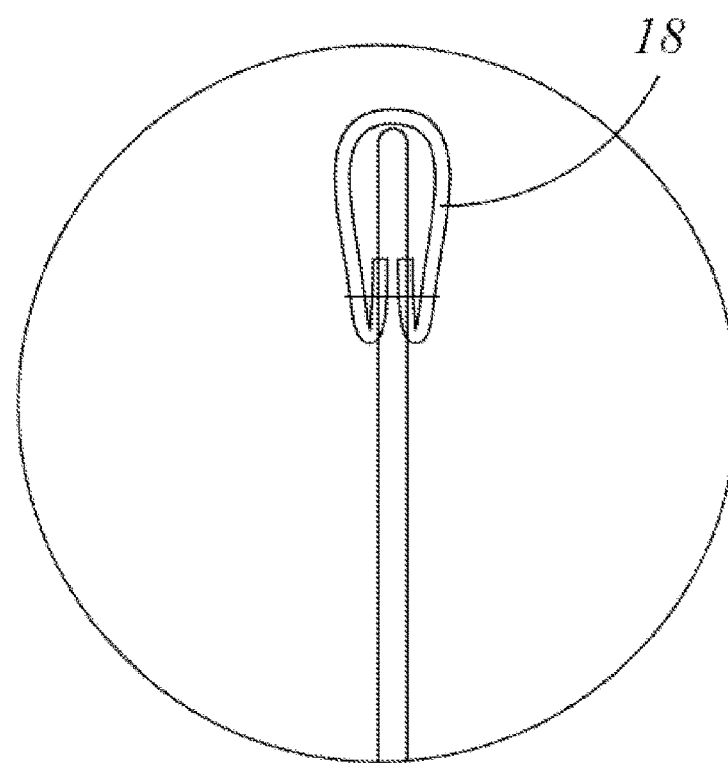
FIG. 27 is a schematic view of a closure edge structure of the fixing device of FIG. 23.

In addition, the front sheet 10f consists of an inner layer and an outer layer, and at least partial edge of the charger fixing seat is connected between the inner layer and outer layer so that the fixing device does not affect the patient's body when worn. In addition, the edge of each of the front sheet 10f, the rear sheet 20f and the charger fixing seat 40f may be provided with a closure edge structure 18 to make the patient more comfortable while wearing the fixing device and meanwhile make the appearance more aesthetic. In addition, as shown in FIG. 24 and FIG. 25, the overall length L of the front sheet and rear sheet is substantially in a range of 200-250 mm, and the front sheet and rear sheet may also be made of a mesh-like fabric, no matter whether the fabric is elastic or not. The left connecting portion and right connecting portion disposed under the armpit has a length substantially in a range of 80-120 mm, and a width in a range of 30-50 mm. The shoulder supporting portion has a length substantially in a range of 90-130 mm and a width in a range of 30-50 mm. The adjustment strap has a length substantially in a range of 360-440 mm and a width in a range of 30-50 mm.

It should be understood that although the description is described according to the embodiments, not every embodiment only includes one independent technical solution, that such a description manner is only for the sake of clarity, that those skilled in the art should take the description as an integral part, and that the technical solutions in the embodiments may be suitably combined to form other embodiments understandable by those skilled in the art.

The detailed descriptions set forth above are merely specific illustrations of feasible embodiments of the present invention, and are not intended to limit the scope of protection of the present invention. All equivalent embodiments or modifications that do not depart from the art spirit of the present invention should fall within the scope of protection of the present invention.

What is claimed is:

1. A fixing device of a wireless charger for an implanted medical device, wherein the fixing device comprising a supporting member wearable on a patient's body and an adjustment structure connected to the supporting member, a charger fixing seat is connected to one of the supporting member and the adjustment structure, the adjustment structure comprises an adjustment strap and a fixing buckle engaging with the adjustment strap, one end of the adjustment strap is connected to the supporting member, the other end of the adjustment strap operably brings the supporting member or the charger fixing seat to be adjusted to a position where the charger fixing seat corresponds to the implanted medical device, and to a position where the adjustment strap engages with the fixing buckle to be adjusted and locked;
    wherein the charger fixing seat is connected to the supporting member, one end of the fixing buckle is fixed on the supporting member, and the other end of the fixing buckle is movably connected to the adjustment strap;
    wherein the supporting member comprises a supporting portion, a shoulder supporting portion, a left connecting portion and a right connecting portion, bottom sides of a front portion of the supporting member and a rear portion of the supporting member are connected via the left connecting portion and the right connecting portion, the shoulder supporting portion is connected between a front portion of the supporting member and a rear portion of the supporting member, the shoulder supporting portion is not provided with any buckle, one of the left connecting portion and the right connecting portion is used to form a shoulder cuff together with the supporting portion and the shoulder supporting portion of the supporting member to be supported under the patient's armpit, the other of the left connecting portion and the right connecting portion is configured as the adjustment strap, the one end of the adjustment strap is connected to the rear portion of the supporting member, and the fixing buckle is connected between the front portion of the supporting member and the adjustment strap.

2. The fixing device of a wireless charger according to claim 1, wherein a shoulder portion of the supporting member and one of the left connecting portion and the right connecting portion are both configured as elastic extensible belts.

3. The fixing device of a wireless charger according to claim 1, wherein the charger fixing seat is configured as a storage bag, and the storage bag is connected between the shoulder of the supporting member and the front portion of the supporting member.

4. The fixing device of a wireless charger according to claim 3, wherein the storage bag comprises an outer bag located outside and an inner bag located inside, a partition layer is disposed between the outer bag and inner bag, and the shoulder portion of the supporting member is connected to the partition layer.

5. The fixing device of a wireless charger according to claim 3, wherein the storage bag comprises an outer bag located outside and an inner bag located inside, and the outer bag is communicated with the inner bag.

6. The fixing device of a wireless charger according to claim 3, wherein a female hook-and-loop fastener belt is disposed on one of an outer side of the storage bag and an inner side of the storage bag, a male hook-and-loop fastener belt having a fluffy surface is disposed on the other of the outer side of the storage bag and inner side of the storage bag, and the female hook-and-loop fastener belt separably engages with the male hook-and-loop fastener belt to close at least one portion of a bag mouth of the storage bag.

7. The fixing device of a wireless charger according to claim 3, wherein one of an outer side of the storage bag and a shoulder portion of the supporting member is provided with a female hook-and-loop fastener belt, the other of the outer side of the storage bag and the shoulder portion of the supporting member is provided with a male hook-and-loop fastener belt having a fluffy surface, and the female hook-and-loop fastener belt separably engages with the male hook-and-loop fastener belt to close at least one portion of a bag mouth of the storage bag.

8. The fixing device of a wireless charger according to claim 1, wherein a front portion of the supporting member consists of an inner layer and an outer layer, and at least partial edge of the charger fixing seat is connected between the inner layer and outer layer.

9. The fixing device of a wireless charger according to claim 1, wherein the charger fixing seat is disposed on the adjustment strap, one end of the adjustment strap is connected to a shoulder portion or a rear portion of the supporting member, the other end of the adjustment strap operably brings the charger fixing seat to be adjusted to a position where the charger fixing seat corresponds to the implanted medical device, and the other end of the adjustment strap is adjusted and locked at the front portion of the supporting member.

10. A wireless charging device, wherein the wireless charging device comprises a wireless charger and the fixing device of the wireless charger according to claim 1, the wireless charger is detachably mounted to the charger fixing seat, and the wireless charger can generate a charging field to charge the implanted medical device.

11. A fixing device of a wireless charger for an implanted medical device, wherein the fixing device comprising a supporting member wearable on a patient's body and an adjustment structure connected to the supporting member, a charger fixing seat is connected to one of the supporting member and the adjustment structure, the adjustment structure comprises an adjustment strap and a fixing buckle engaging with the adjustment strap, one end of the adjustment strap is connected to the supporting member, the other end of the adjustment strap operably brings the supporting member or the charger fixing seat to be adjusted to a position where the charger fixing seat corresponds to the implanted medical device, and to a position where the adjustment strap engages with the fixing buckle to be adjusted and locked; wherein the charger fixing seat is disposed on the adjustment strap, one end of the adjustment strap is connected to a shoulder portion or a rear portion of the supporting member, the other end of the adjustment strap operably brings the charger fixing seat to be adjusted to a position where the charger fixing seat corresponds to the implanted medical device, and the other end of the adjustment strap is adjusted and locked at the front portion of the supporting member;
wherein the supporting member comprises a left connecting portion and a right connecting portion, bottom sides of a front portion of the supporting member and a rear portion of the supporting member are connected via the left connecting portion and the right connecting portion, the left connecting portion and the right connecting portion are respectively used to form a shoulder cuff to be supported under the patient's armpit, one end of the adjustment strap is connected to the shoulder portion of the supporting member or the rear portion of the supporting member, and the other end of the adjustment strap is adjusted and locked at the front portion of the supporting member;
wherein the front portion of the supporting member is provided with a charging opening, the charging opening corresponds to a position of the implanted medical device, and the charger fixing seat is adjusted in the charging opening.

12. The fixing device of a wireless charger according to claim 11, wherein the adjustment strap comprises a positioning strap connecting the shoulder portion of the supporting member or the rear portion of the supporting member and the charger fixing seat and a fixing strap connecting the charger fixing seat with the front portion of the supporting member, and the fixing strap is adjusted and locked at the front portion of the supporting member.

13. The fixing device of a wireless charger according to claim 12, wherein the positioning strap is configured as an elastic extensible belt or provided with a length adjuster, and the length adjuster moves in a lengthwise direction of the positioning strap to adjust a distance between a connection end of the positioning strap connected to the supporting member and the charger fixing seat.

14. The fixing device of a wireless charger according to claim 12, wherein the fixing buckle comprises a female hook-and-loop fastener belt and a male hook-and-loop fastener belt engaging therewith and having a fluffy surface, the female hook and loop fastener belt is disposed on one of the fixing strap and the front portion of the supporting member, the male hook-and-loop fastener belt is disposed on the other of the fixing strap and the front portion of the supporting member, and the fixing strap is adjusted and locked through the separable engagement of the female hook-and-loop fastener belt and the fluffy surface to adjust the position of the charger fixing seat.

15. The fixing device of a wireless charger according to claim 12, wherein the positioning strap is connected to a middle portion of the rear portion of the supporting member via a fixing snap and is rotatable relative to the supporting member.

16. The fixing device of a wireless charger according to claim 11, wherein the front portion of the supporting member comprises a left front sheet and a right front sheet, and the left front sheet and right front sheet are both provided with a charging opening and separably connected.

17. The fixing device of a wireless charger according to claim 16, wherein the left front sheet and right front sheet are overlappable left and right and connected in a hook-and-loop manner, and wherein an outer side of one of the left front sheet and right front sheet is provided with a first male hook-and-loop fastener belt having a fluffy surface, an inner side of the other of the left front sheet and right front sheet is provided with a female hook-and-loop fastener belt engaging with the fluffy surface, an outer side is provided with a second male hook-and-loop fastener belt having the fluffy surface, and the other end of the adjustment strap is separably connected to the second male hook-and-loop fastener belt.

* * * * *